(12) United States Patent
Kelley et al.

(10) Patent No.: US 6,836,687 B2
(45) Date of Patent: Dec. 28, 2004

(54) METHOD AND SYSTEM FOR DELIVERY OF A MEDICAL ELECTRICAL LEAD WITHIN A VENOUS SYSTEM

(75) Inventors: James F. Kelley, Coon Rapids, MN (US); James H. Vaughn, Blaine, MN (US); Stanten C. Spear, Arden Hills, MN (US); Douglas S. Hine, White Bear Lake, MN (US); Kenneth C. Gardeski, Plymouth, MN (US); Vicki L. Bjorklund, Maple Grove, MN (US); Pedro A. Meregotte, Vadnais Heights, MN (US); John L. Sommer, Coon Rapids, MN (US); John J. Maier, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 1 day.

(21) Appl. No.: 10/131,388

(22) Filed: Apr. 25, 2002

(65) Prior Publication Data

US 2002/0165536 A1 Nov. 7, 2002

Related U.S. Application Data

(63) Continuation-in-part of application No. 09/822,678, filed on Mar. 30, 2001, now Pat. No. 6,743,227.
(60) Provisional application No. 60/193,695, filed on Mar. 31, 2000.

(51) Int. Cl.[7] .................................................. A61N 1/05
(52) U.S. Cl. ..................... 607/122; 607/115; 607/116; 607/114; 607/119; 600/374
(58) Field of Search ....................... 606/1, 41; 607/115, 607/116, 114, 122, 126; 604/164.01, 164.02, 164.13, 264

(56) References Cited

U.S. PATENT DOCUMENTS

| | | |
|---|---|---|
| 4,215,703 A | 8/1980 | Willson |
| 4,813,434 A | 3/1989 | Buchbinder et al. |
| 4,911,148 A | 3/1990 | Sosnowski et al. |
| 5,304,131 A | 4/1994 | Paskar |
| 5,312,355 A | 5/1994 | Lee |
| 5,441,483 A | 8/1995 | Avitall |
| 5,507,725 A | 4/1996 | Savage et al. |
| 5,509,411 A | 4/1996 | Littmann et al. |
| 5,645,064 A | 7/1997 | Littmann et al. |
| 5,645,082 A | 7/1997 | Sung et al. |
| 5,682,885 A | 11/1997 | Littmann et al. |
| 5,699,796 A | 12/1997 | Littmann et al. |
| 5,701,298 A | 12/1997 | Diachina et al. |
| 5,706,809 A | 1/1998 | Littmann et al. |
| 5,711,298 A | 1/1998 | Littmann et al. |
| 5,766,152 A | 6/1998 | Morley et al. |
| 5,775,327 A | 7/1998 | Randolph et al. |

(List continued on next page.)

FOREIGN PATENT DOCUMENTS

| | | |
|---|---|---|
| EP | 0801955 A1 | 4/1996 |
| EP | 1060757 A1 | 5/2000 |
| FR | 2804608 A1 | 2/2000 |
| FR | 2809016 A1 | 5/2000 |
| WO | WO02/04062 A2 | 1/2002 |

*Primary Examiner*—Rosiland Rollins
(74) *Attorney, Agent, or Firm*—Michael C. Soldner; Girma Wolde-Michael

(57) ABSTRACT

A system for delivering a medical electrical lead within a coronary venous system that includes an introducer kit for establishing venous access to the coronary venous system and a plurality of delivery sheaths, each corresponding to a desired approach to a coronary sinus of the coronary venous system and insertable within the coronary venous system through the navigation pathway. A hemostasis valve is coupled to a delivery sheath of the plurality of delivery sheaths, and a guide wire is inserted within the lead lumen, guiding delivery of the distal tip of the medical electrical lead to a target site within the coronary venous system through the hemostasis valve and the delivery sheath. Subsequent to the distal tip being delivered to the target sight, the hemostasis valve is advanced over the connector of the medical electrical lead to remove the hemostasis valve from the medical electrical lead.

18 Claims, 36 Drawing Sheets

U.S. PATENT DOCUMENTS

| | | |
|---|---|---|
| 5,782,760 A | 7/1998 | Schaer |
| 5,824,031 A | 10/1998 | Cookston et al. |
| 5,827,296 A * | 10/1998 | Morris et al. ............... 606/129 |
| 5,863,291 A | 1/1999 | Schaer |
| 5,868,768 A | 2/1999 | Wicherski et al. |
| 5,881,732 A | 3/1999 | Sung et al. |
| 5,882,333 A | 3/1999 | Schaer et al. |
| 5,885,238 A | 3/1999 | Stevens et al. |
| 5,902,289 A | 5/1999 | Swartz et al. |
| 5,921,924 A | 7/1999 | Avitall |
| 5,967,978 A | 10/1999 | Littmann et al. |
| 6,002,956 A | 12/1999 | Schaer |
| 6,021,340 A | 2/2000 | Randolph et al. |
| 6,122,552 A | 9/2000 | Tockman et al. |
| 6,192,280 B1 | 2/2001 | Sommer et al. |
| 2001/0005783 A1 | 6/2001 | Hassett |

* cited by examiner

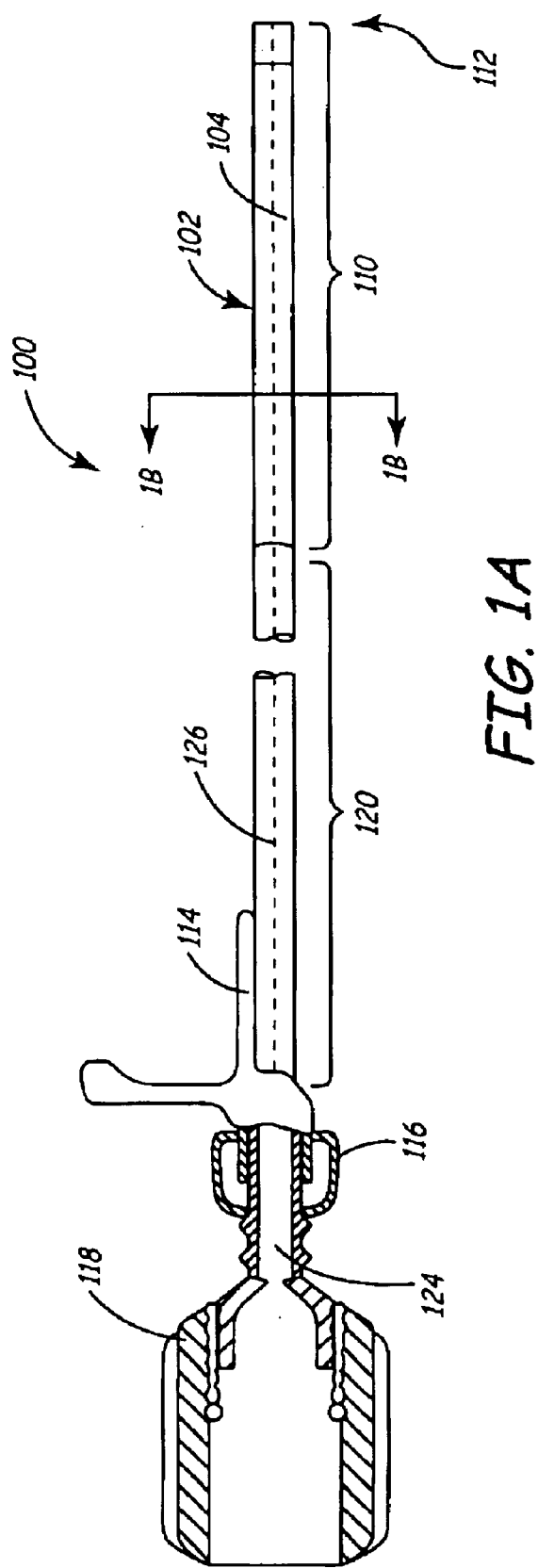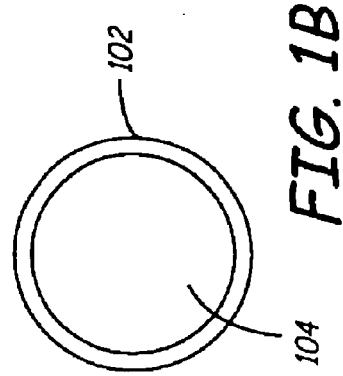

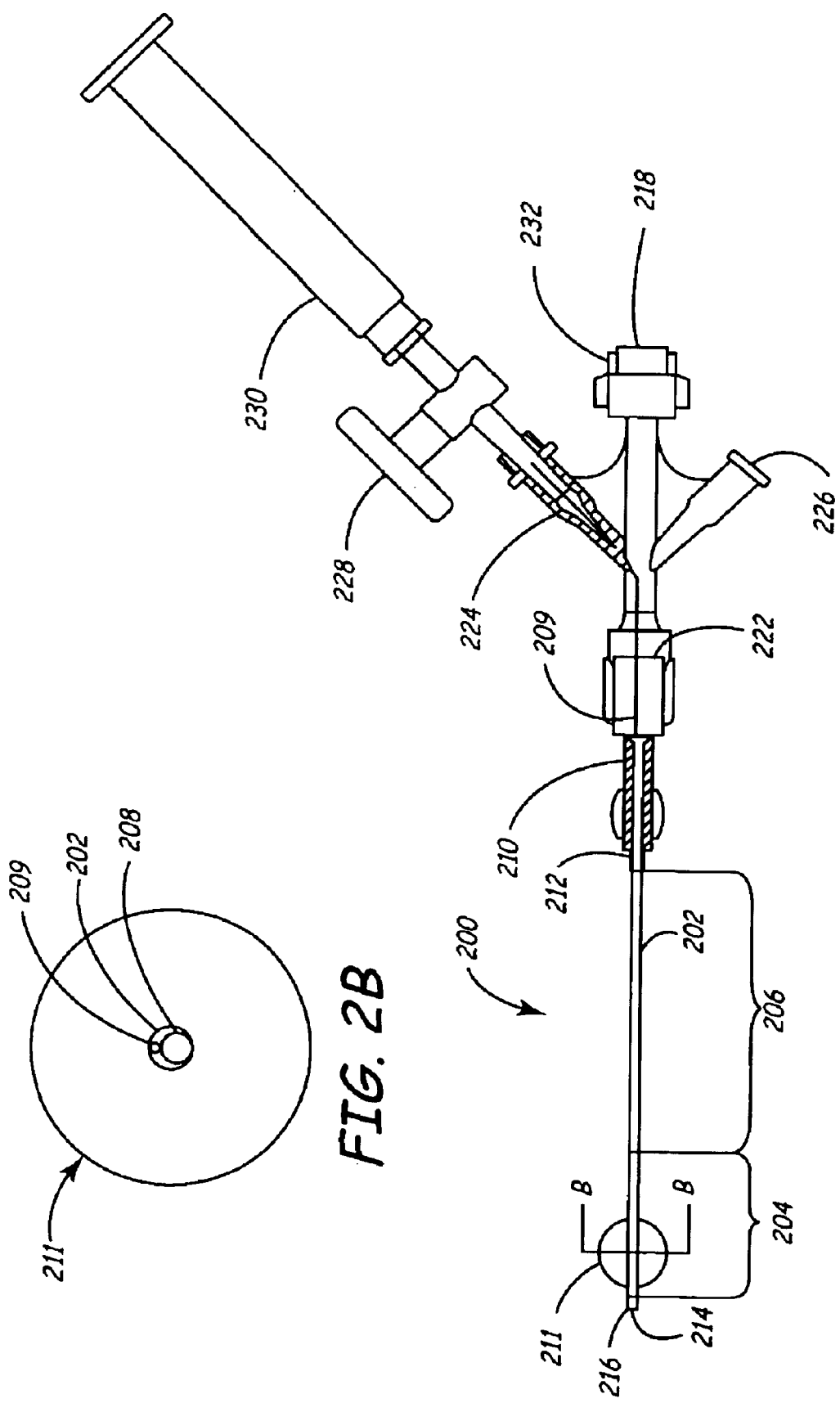

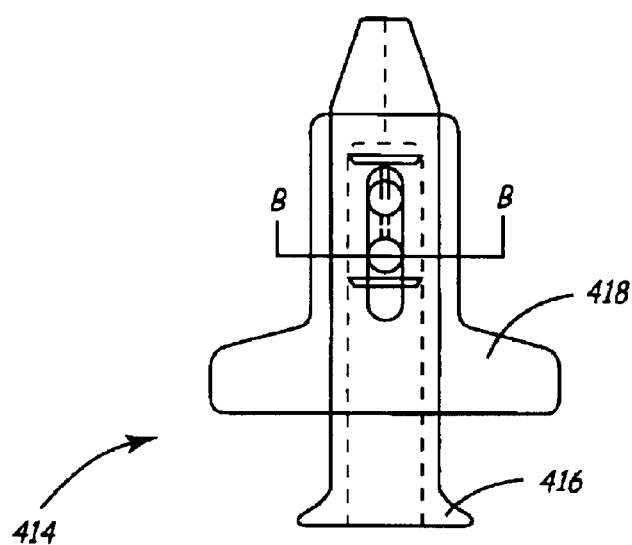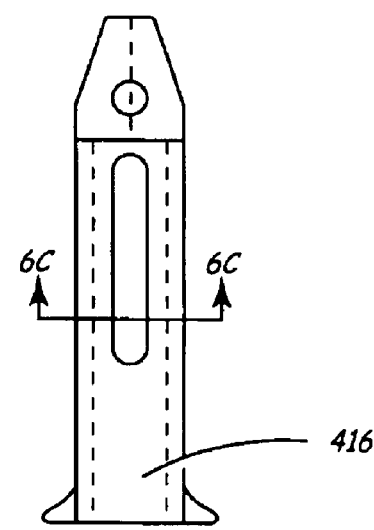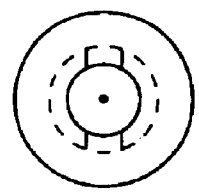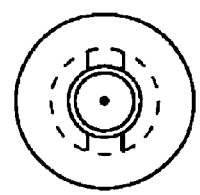
FIG. 6A
FIG. 6D
FIG. 6B
FIG. 6C

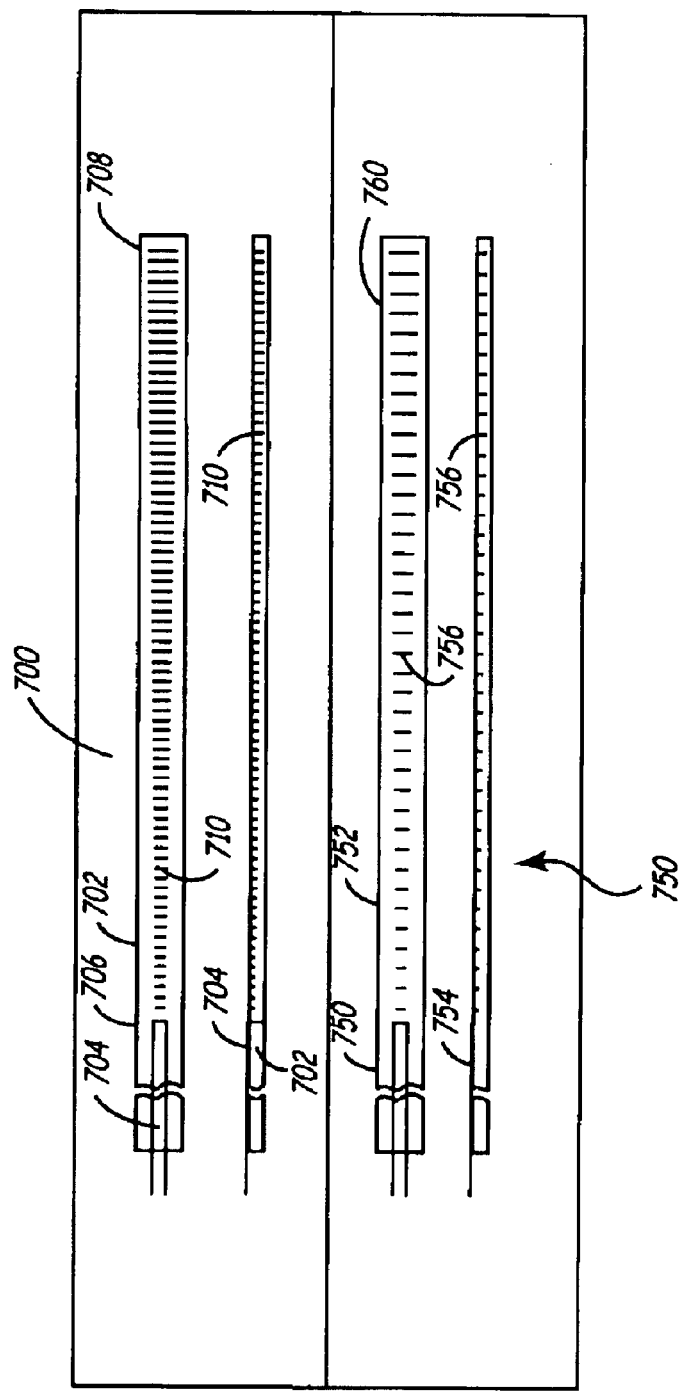

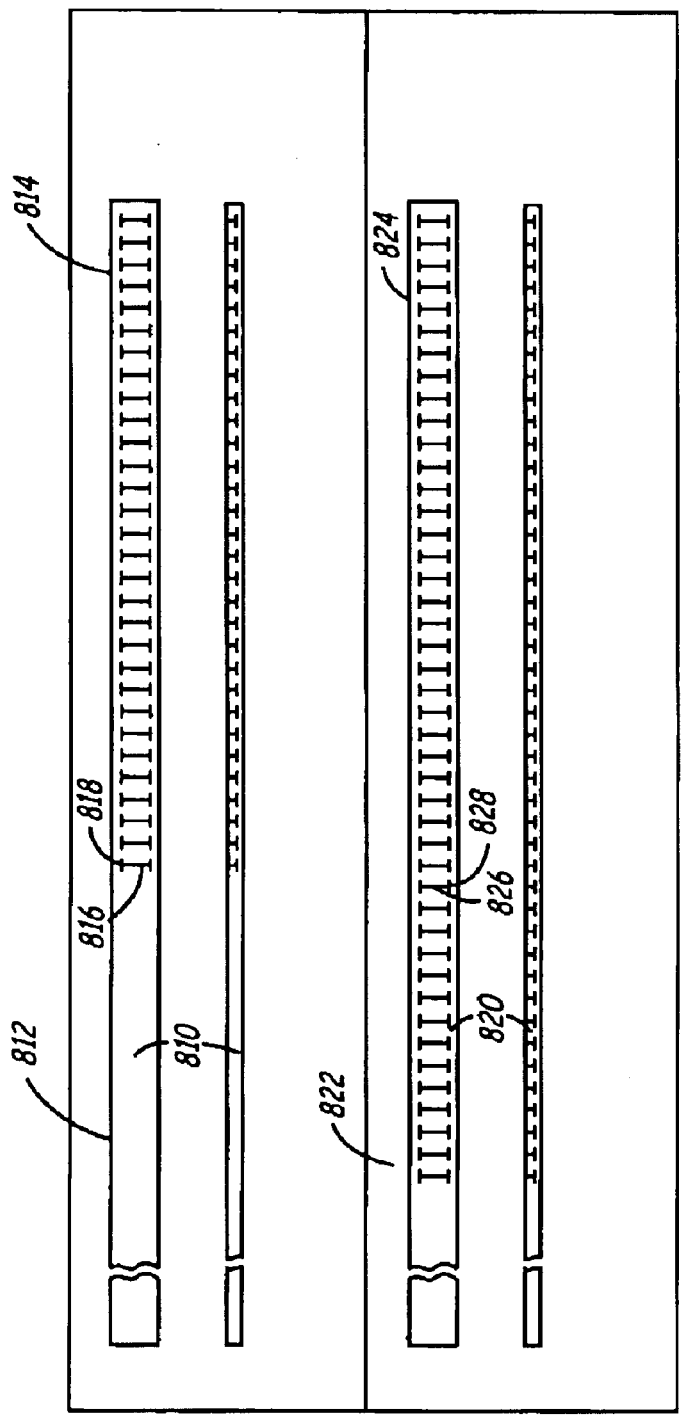

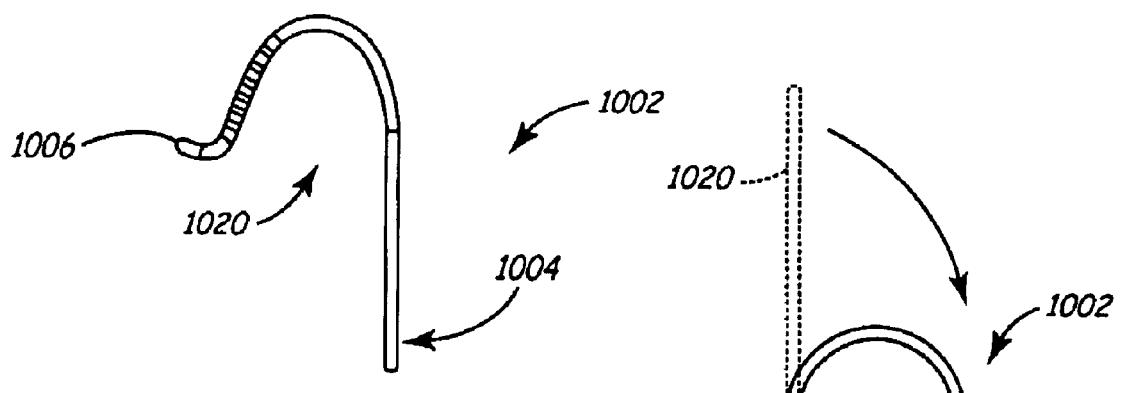
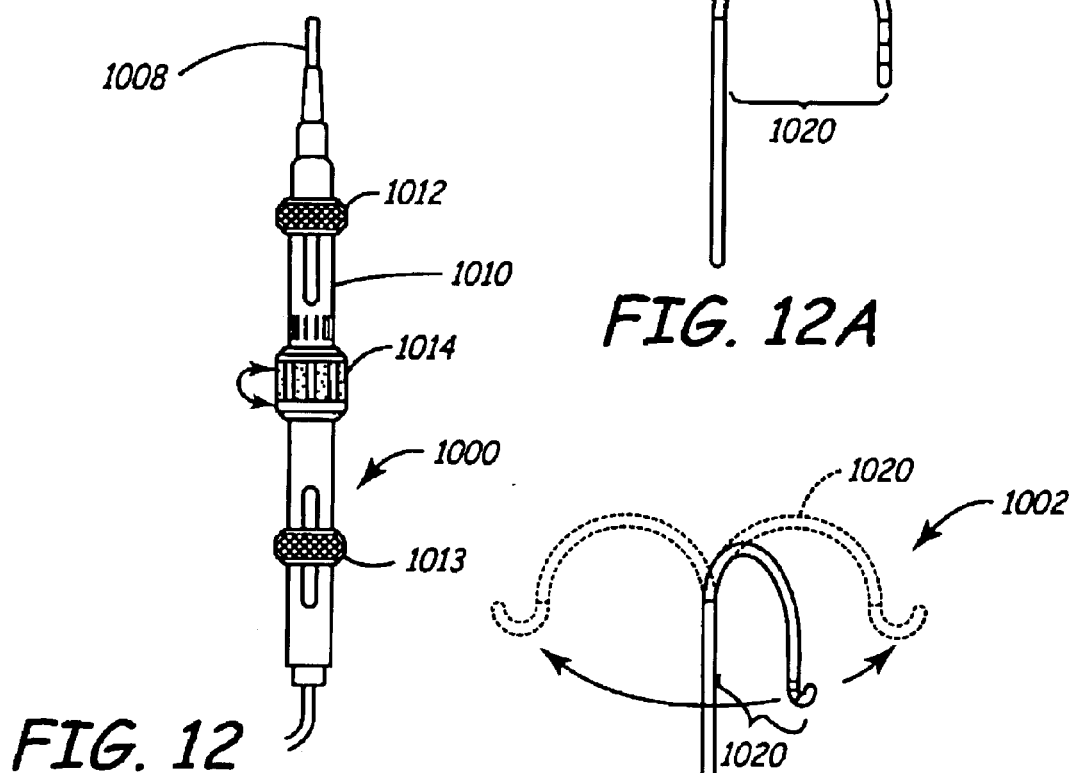
FIG. 12A
FIG. 12
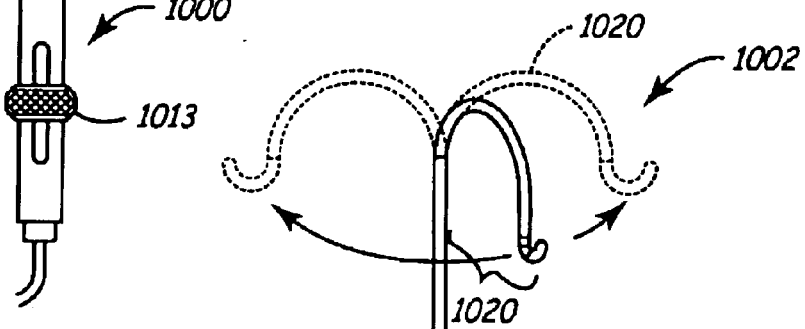
FIG. 12C
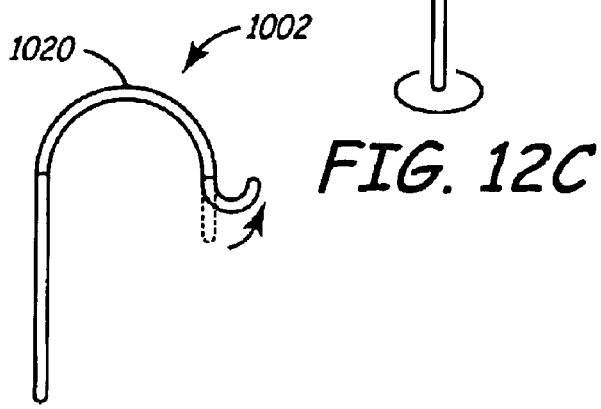
FIG. 12B

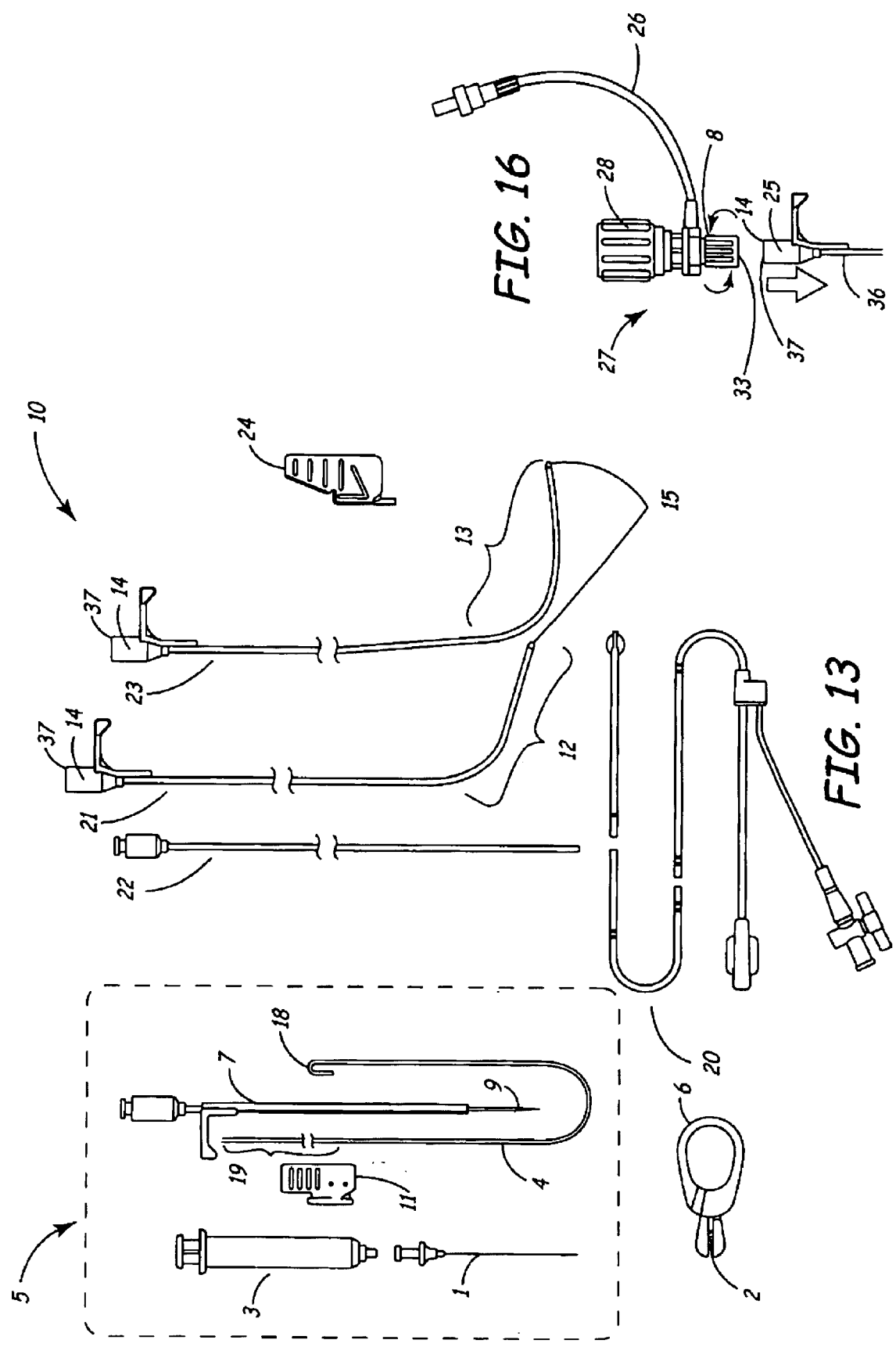

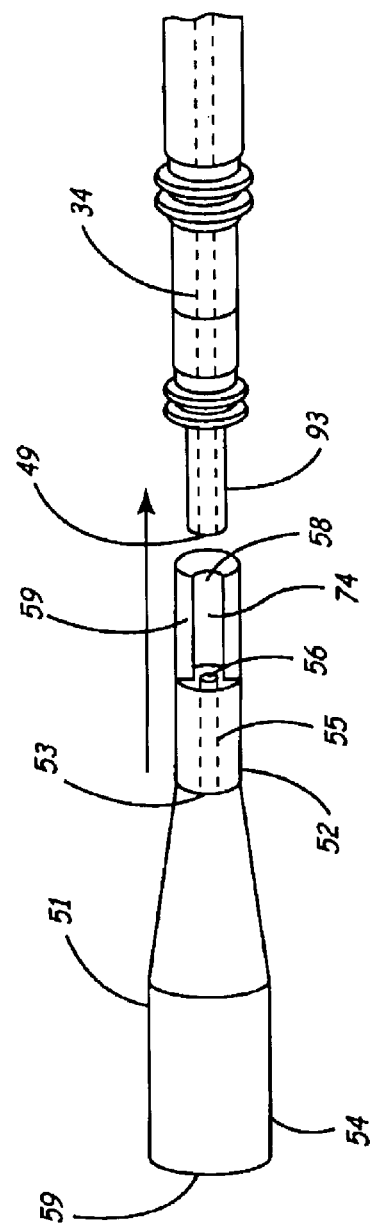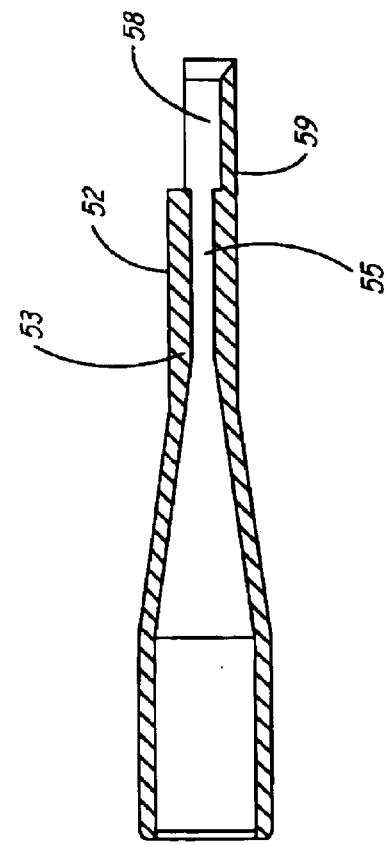
FIG. 24
FIG. 25

METHOD AND SYSTEM FOR DELIVERY OF A MEDICAL ELECTRICAL LEAD WITHIN A VENOUS SYSTEM

RELATED APPLICATIONS

This application is a continuation-in-part of commonly assigned U.S. patent application Ser. No. 09/822,678 filed Mar. 30, 2001 now U.S. Pat. No. 6,743,227, which is related to, and claims the benefit of provisionally-file U.S. Patent Application No. 60/193,695, filed Mar. 31, 2000, and entitled "Intraluminal Visualization System with Deflectable Mechanism", both of which are incorporated herein by reference in their entireties.

Cross-reference is hereby made to commonly assigned related U.S. Applications, filed concurrently herewith, docket number P-10017.02 CIP1, entitled "IMPROVED SYSTEM AND METHOD FOR POSITIONING IMPLANTABLE MEDICAL DEVICES WITHIN CORONARY VEINS", and docket number P-10017.04 CIP3, entitled "METHOD AND SYSTEM FOR DELIVERING A MEDICAL ELECTRICAL LEAD WITHIN A VENOUS SYSTEM".

BACKGROUND OF THE INVENTION

The present invention relates generally to delivery of various devices or agents into a targeted area of the body, and in particular, the present invention relates to a method and system for accurately delivering medical devices such as leads, electrophysiology catheters, and therapeutic agents into large-organ vessel systems such as the coronary vasculature.

In treating conditions such as arrhythmia, one technique is to destroy or damage heart tissue that causes or is involved with the arrhythmia by suitably heating the tissue, e.g., by applying a laser beam or high-frequency electrical energy such as radio-frequency (RF) or microwave energy.

For such treatment to be effective, the location of the tissue site causing or involved with the arrhythmia must be accurately determined in order to be able to contact heart tissue adjacent the desired location with a tissue-destroying device. A high degree of accuracy in determining this site is paramount so that an excessive amount of viable tissue is not destroyed adjacent the site. For example, the average arrhythmogenic site consists of about 1.4 $cm^2$ of endocardial tissue, whereas a re-entrant site might be much larger. RF ablation techniques produce lesions about 0.5 $cm^2$ of diameter, so a number of lesions are typically generated in order to ablate the area of interest. If the site is not accurately mapped, much of the viable tissue surrounding the site will be unnecessarily destroyed.

To determine the location of the tissue to be ablated, it is widely known to use elongated intravascular signal sensing devices that are advanced through the patient's vasculature until the distal portions of the device are disposed within one or more of the patient's heart chambers, with one or more electrodes on the distal portion of the device in contact with the endocardial lining. Such devices may also be advanced within a patient's coronary artery, coronary sinus, or cardiac vein. Sensing devices such as those disclosed in U.S. Pat. No. 5,967,978 to Littmann et al., and combination sensing-ablation devices such as those disclosed in U.S. Pat. No. 6,002,956 to Schaer are typical.

Guiding catheters such as those disclosed in U.S. Pat. Nos. 6,021,340 and 5,775,327 to Randolph et al. may be used to rapidly advance such devices into a patient's cardiac vein draining into the coronary sinus. A particular advantage of the catheters disclosed in these references is the presence of an inner lumen and distal port on the catheter shaft, which, in conjunction with a distal balloon, allows for the deployment of contrast fluid distal to the distal end of the catheter for visualizing the venous structure.

The following U.S. Patents discuss related devices and methods for their use: U.S. Pat. Nos. 5,509,411, 5,645,064, 5,682,885, 5,699,796, 5,706,809, and 5,701,298, each to Littmann et al; U.S. Pat. Nos. 5,881,732 and 5,645,082, each to Sung et al; U.S. Pat. No. 5,766,152 to Morely et al; U.S. Pat. Nos. 5,782,760 and 5,863,291, each to Schaer; U.S. Pat. No. 5,882,333 to Schaer et al., and U.S. Pat. No. 6,122,552 to Tockman et al.

However, despite the advantages of these sensing devices and guiding catheters, it remains quite difficult to accurately and reliably contact the various curved shapes one encounters in the endocardial lining. This is due to the frequent inability to customize the shape of their distal portion, or at least the inability to instantaneously and accurately adjust their shape upon demand during deployment to conform to the shape of the tissue of interest.

Concerns similar to those described above are associated with the placement of leads within the heart and other areas of the coronary vasculature. For example, pacemakers, defibrillator/cardioverters, and other implantable medical device (IMDs) may employ one or more electrodes that are maintained in contact with a patient's heart muscle and through which electrical stimulation of the heart muscle is achieved. Such devices typically employ a flexible conductive lead that connects a remotely positioned and implanted power source to the one or more electrodes. Secure placement of the electrodes in the selected heart chamber (typically the right atrium) or in a coronary vein or artery is required to assure appropriate and reliable depolarization or "capture" of cardiac tissue by electrical stimuli delivered by the IMD.

Many problems exist with reliably and accurately placing medical electrical leads and other similar devices such as catheters within the heart and associated vasculature. For instance, when placing transvenous leads or catheters, it is often difficult to engage the coronary sinus and sub-select the proper vessel into which the lead or catheter is to eventually be placed. Moreover, once placed, transvenous devices suffer from a relatively high rate of dislodgment from sites adjacent to, or on, the epicardium. Such dislodgement may result in a loss of capture or, at best, a reduction of the degree of electrical coupling between the electrode and the myocardium. More accurate and secure placement of the lead or catheter would not only reduce the difficulty and time associated with lead placement, but would reduce the risk of subsequent dislodgment as well.

There thus is a need for a method and system for placing intralumenally-deployed devices such as electrophysiology catheters and leads into selected areas of the coronary vasculature in a highly accurate and reliable fashion.

SUMMARY OF THE INVENTION

The present invention is directed to a system for delivering a medical electrical lead within a coronary venous system that includes an introducer kit for establishing venous access and a plurality of delivery sheaths, each corresponding to a desired approach to a coronary sinus of the coronary venous system and insertable within the coronary venous system through the navigation pathway. A hemostasis valve is coupled to a delivery sheath of the plurality of delivery sheaths, and a guide wire is inserted within the lead lumen, guiding delivery of the distal tip of the medical electrical lead to a target site within the coronary venous system through the hemostasis valve and the delivery sheath. Subsequent to the distal tip being delivered to the target sight, the hemostasis valve is advanced over a connector pin of the medical electrical lead to remove the hemostasis valve from the medical electrical lead.

According to an embodiment of the present invention, a system for delivering a medical electrical lead within a coronary venous system includes an introducer kit that establishes venous access to the coronary venous system, and a plurality of delivery sheaths, each corresponding to a desired approach to a coronary sinus of the coronary venous system and insertable within the coronary venous system through the navigation pathway. An anchoring sleeve is positioned along the medical electrical lead and a hemostasis valve is coupled to a delivery sheath of the plurality of delivery sheaths. A guide wire is inserted within the lead lumen, guiding delivery of the distal tip of the medical electrical lead to a target site within the coronary venous system though the hemostasis valve and the delivery sheath. Subsequent to the distal tip being delivered to the target sight, the hemostasis valve is advanced over a connector pin of the medical electrical lead and the anchoring sleeve of the medical electrical lead to remove the hemostasis valve from the medical electrical lead.

According to yet another embodiment of the present invention, the guide wire is a stylet having a stylet knob, and the hemostasis valve is advanced over the stylet knob to remove the hemostasis valve from the medical electrical lead.

BRIEF DESCRIPTION OF THE DRAWINGS

FIG. 1A is a side cutaway view of a delivery sheath of the present invention.

FIG. 1B is a cross-sectional view of a delivery sheath of the present invention.

FIGS. 2A–2B are side and cross-sectional views, respectively, of a balloon catheter of the present invention.

FIGS. 6A–6D are various views of a micro-deflection mechanism handle of the present invention.

FIGS. 7A–7B are two embodiments of deflection and micro-deflection mechanisms detailing two notch configurations.

FIGS. 8A–8D are additional embodiments of deflection and micro-deflection mechanisms of the present invention, detailing additional notch configurations.

FIG. 12 is a plan view of a steerable catheter that may be used as an alternative deflection mechanism to navigate the balloon catheter 200 into the coronary sinus.

FIGS. 12A through 12C illustrate various deflection positions of the distal tip of the steerable catheter of FIG. 12.

FIG. 13 is a schematic diagram of a tool kit used to establish venous access in a system for delivering medical devices within a coronary venous system according to the present invention.

FIG. 16 is a schematic diagram of a rotatable hemostasis valve (RHV) of a tool kit according to the present invention.

FIG. 24 is a schematic diagram of a loading tool in a system for delivering medical devices within a venous system according to the present invention.

FIG. 25 is a cross-sectional view of the loading tool of FIG. 24.

DETAILED DESCRIPTION OF THE INVENTION

Figure 3:
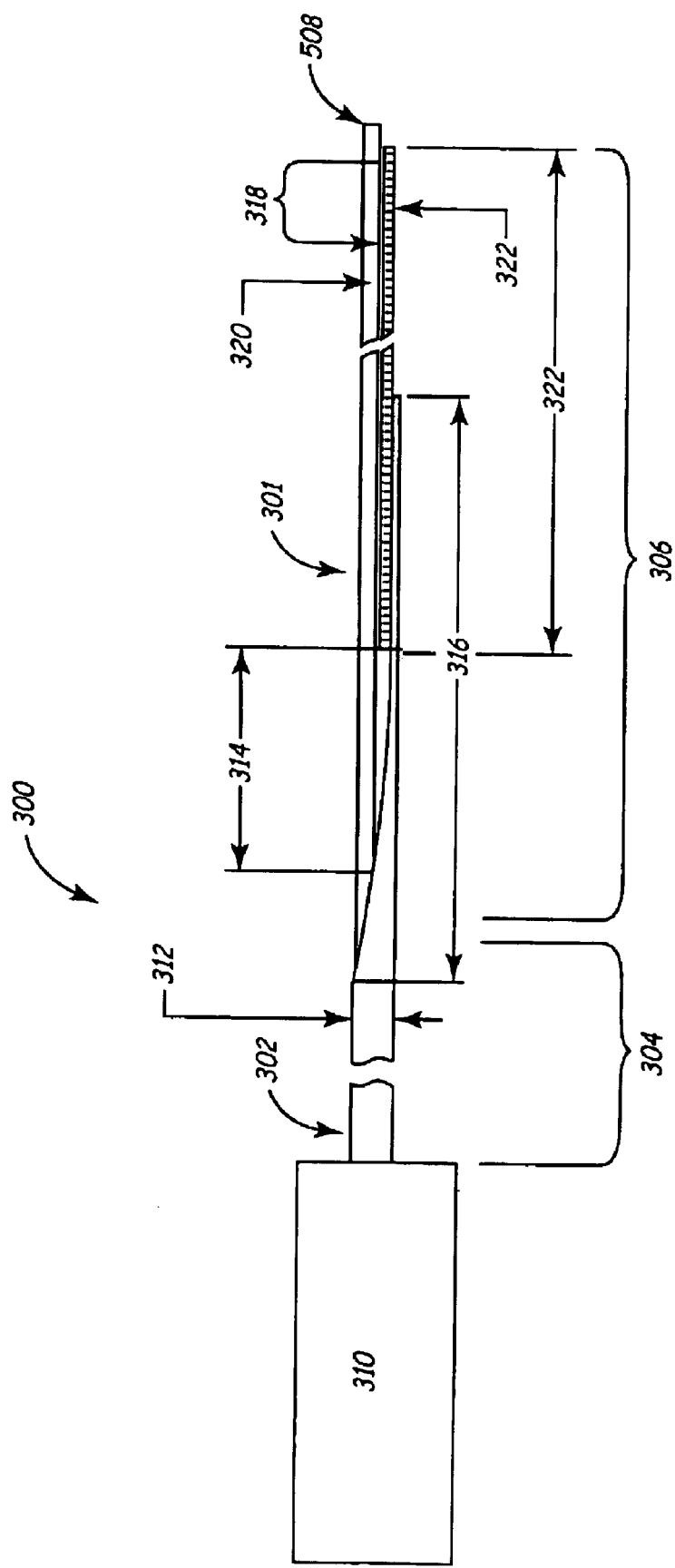
FIG. 3 is as side view illustrating components included in both the deflection mechanism and micro-deflection mechanism of the present invention.

This invention is a method and system for intralumenal visualization and deployment of implantable medical devices (IMDs) such as transvenous leads, electrophysiology catheters and the like to various targeted regions of the body. The inventive system includes a sheath, a balloon catheter and associated deflection mechanism, and a micro-deflection device for highly accurate placement of the lead, catheter, or other device once the area of interest has been visualized.

In the following pages we provide a component-by-component description of a preferred variation of the invention followed by a description of a procedure for using this system to place a transvenous lead into the coronary veins. Although we detail an exemplary set of system components and a method for its use, additional system configurations, adaptations, and methods of use, some of which are also described herein, are within the scope of the invention.

In general, the intralumenal visualization system and micro-deflection device of the present invention includes a deflectable catheter that includes an inflatable member such as a balloon, and is insertable into a lumen of a delivery sheath. This sheath may be inserted into the body via a typical introducer as will be described in more detail. In a preferred use, a balloon catheter is guided by a deflection mechanism so that it may engage the coronary sinus ostium. A balloon catheter is inserted through the delivery sheath and into the coronary sinus or through a delivery sheath over a guide wire so that an occlusive venogram may be rendered and the balloon catheter is removed. Next, a lead with a micro-deflection mechanism is inserted into the sheath lumen so that the lead may be deployed at the desired location in the coronary veins. The micro-deflection mechanism disposed within the lead is used to provide rigidity to the lead and to allow a means to sub-select coronary vessels. The sheath preferably may be splittable along its longitudinal length so that it may be removed around the lead without disturbing it.

Delivery Sheath

FIG. 1A is a cutaway side view depicting a variation of the delivery sheath described above. As best seen in FIG. 1A, sheath 100 comprises an elongate shaft 102 containing a central lumen 104 throughout its length. The working length of sheath 100 comprises a distal section 110 and a proximal section 120, each of which comprises a polymeric material having differing flexibilities as described below. A distal end 112 of sheath 100 disposed adjacent distal section 110 also comprises the working length.

Near the proximal end of sheath 100, a hub 114 may be affixed to proximal section 120 by an adhesive or other suitable means. We prefer an ultraviolet-curable adhesive sold by Loctite Corp. of Rocky Hill, Conn. under the name UV 4201. We also prefer an adhesive sold by Dymax corp. of Trorrington, Connecticut under the trademark DYMAX. Hub 114 is made from any suitable medical-grade polymer, and is preferably injection molded and longitudinally scored or perforated so that it may be removed from around a device without disturbing that device. It may be molded in situ onto the proximal section 120 of shaft 102.

Hub 114 has an opening large enough to accommodate a special rotatable hemostatic valve (RHV) 118, to which it is detachably secured by, e.g., an annular ring on the valve 118 inner diameter. A central lumen 124 in RHV 118 is aligned and in fluid communication with the lumen of shaft 102. Lumen 124 has a diameter large enough to accommodate a balloon catheter and a typical lead connector, such as an IS-1-type connector. An optional side arm (not shown) may be disposed on RHV 118 in fluid communication with lumen 124. RHV 118 may also be splittable via a scoring or perforation as described above.

An annular polymeric collar 116 is disposed on the outside diameter of RHV 118 distal portion proximal to the point where hub 114 meets RHV 118. In this embodiment, rotation of collar 116 locks the RHV 118 to the hub 114.

FIG. 1B is a cross-sectional view of the delivery sheath of FIG. 1A. As shown in FIG. 1B, a cross-section of shaft 102 in the distal section 110 reveals shaft lumen 104. The inner diameter of shaft 102 will vary depending on the outer diameter of the balloon catheter and the lead, each of which should be capable of passing through lumen 104. Typically the shaft inner diameter is between about 0.080 and 0.110 inch; more preferably it is about 0.098 inch. Likewise, the outer diameter of shaft 102 is typically between about 0.090 and 0.130 inch; more preferably it is about 0.118 inch. We prefer the outer diameter of shaft 102 to be as small as possible while still maintaining acceptable performance levels according to the application for which the shaft is used. We also prefer that shaft 102 generally maintains a constant inner diameter throughout its length to provide a smooth and continuous step-free profile for the passage of various devices and materials therethrough as described herein.

Tubing comprising distal section 110 and proximal section 120 will typically be polymeric, and is preferably any typical medical grade, biocompatible tubing with the appropriate performance characteristics as described herein. An especially desirable material is an extruded polyether block amide of the type sold by Atochem North America, Inc., Philadelphia, Pa. under the trademark PEBAX.

Distal and proximal sections 110 and 120, respectively, are constructed of tubing having a durometer hardness ranging from about 20D to 100D (shore). The working length of shaft 102 preferably is composed of materials having two or more stiffnesses, although shaft 102, having a single stiffness value throughout its length is within the scope of the invention.

In one embodiment, proximal section 120 comprises a relatively high stiffness material (typically about 72D) in comparison to the more flexible distal section 110 (typically about 40D). Although not shown in the view of FIG. 1B, distal section 110 and proximal section 120 may be comprised of a DACRON (E.I. du Pont de Nemours and Company, Wilmington, Del.) braid with a TEFLON (E.I. du Pont de Nemours and Company, Wilmington, Del.) liner. The braid is surrounded by the PEBAX tubing as described above, which renders the proximal section 120 of shaft 102 generally stiffer and less flexible than distal portion 110.

Distal end 112 is preferably a soft, atraumatic tip made form a relatively low stiffness polymeric material so to prevent injury to the intima of the vessel walls or to other tissue. We have found an effective material for distal end 112. A material well-suited for the distal end is a thermoplastic polyurethane elastomer such as PELLETHANE (Dow Chemical Co., Midland, Mich.) or the like.

According to one aspect of the invention, distal portion 110 may be radiopaque. This can be achieved by the inclusion of radiopaque metals or their alloys into the structure, or more preferably by incorporating radiopaque powders such s BaSO, BiCO, etc. into the polymer comprising distal portion 110. Distal end 112 is preferably more radiopaque than distal portion 110. This can be achieved by the incorporation of greater quantities of radiopaque powder, for instance, into the tubing, or by the use of a different material having greater radiopacity than that used in distal portion 110. This radiopaque feature allows the user to more readily visualize these portions of sheath 100 under fluoroscopy.

The entire length of shaft 102 (from distal end 112 to the far proximal end of RHV 118) is typically between about 40 and 60 cm, and is preferably about 55 cm. Distal end 112 may be between about 0.2 cm and 0.5 cm long, while distal section 110 is generally between about 5 and 10 cm long, and is preferably about 8 cm long. Proximal section 120 is between about 35 and 50 cm long; preferably about 42 cm.

Both the working length of shaft 102 as well as the attached hub 114 may contain a perforation or score 126 along their longitudinal axes. Alternatively, they may be otherwise configured to split so that they may be opened and removed from around an inserted device such as a lead or electrophysiology catheter without having to axially slide the sheath 100 relative to the device. A special tool may be used to facilitate such splitting, or the sheath/hub (and even RHV 114) combination may be split by hand without the aid of any special device. The splittable valve and sheath combinations as described in U.S. Pat. No. 5,312,355 to Lee is exemplary.

Balloon Catheter

Turning now to FIGS. 2A–2B, a balloon catheter 200 of the present invention is shown in side view and distal cross-sectional view, respectively. This catheter is largely similar to the guiding catheters disclosed in U.S. Pat. Nos. 6,021,340 and 5,775,327 to Randolph et al, the entirety of each of which are incorporated herein by reference, as well as the VUEPORT family of balloon occlusion guiding catheters sold by Cardima, Inc. of Fremont Calif.

Catheter 200 is designed to pass through the central lumen 104 of deployment sheath 100, and reach the therapeutic site as a combined unit with sheath 100 and deflection mechanism 300.

As shown in FIGS. 2A and 2B, balloon catheter 200 generally includes an elongated shaft 202, a distal shaft section 204, a proximal shaft section 206, and an inner lumen 208. A female luer lock 210 may be disposed on the proximal end of shaft 202 and secured by a suitable adhesive 212, such as UV-curable Loctite 4201.

A distal port 214 is provided in the distal end 216 of the catheter shaft that is in fluid communication with the inner lumen 208. Proximal of distal end 216 is an occlusion balloon 211 axially disposed in the distal section 204 about catheter shaft 202. The catheter shaft 202 is provided with an inflation lumen 209 that extends through the shaft 202 to the interior of the balloon 211 to direct inflation fluid therein.

On the proximal end of catheter 200, proximal to luer lock 210, is a multiarm adapter or hub 222 that terminates in a Y-adapter or hemostasis valve 232 and a proximal port 218 for passage of a deflection mechanism therethrough as described later.

A first sidearm or port 224 on adapter 222 (shown in partial cross section in FIG. 2A) facilitates introduction of inflation fluid into inflation lumen 209. A stopcock 228 on first sidearm 224 that allows balloon 221 to stay inflated once the proper volume of fluid (such as air) has been introduced via syringe 230 is disposed adjacent stopcock 228. Inflation lumen 209 is disposed in port 224 and extends distally into shaft 224 to facilitate inflation of balloon 211 as described above.

A second sidearm or port 226 may also be disposed on hub 222, and may be in direct fluid communication with large inner lumen 208. Inner lumen 208 is used for housing devices such as a deflection mechanism or the like. Once balloon 211 is inflated, the second port 226 may be used for introducing contrast media or similar material through lumen 208 and out the distal port 214 for visualization of a section of interest in the body, such as an organ lumen or the cardiac venous system, for instance.

Not shown is a rotatable hemostatic valve (RHV) that may be housed in the proximal center port 218 and that can accept devices such as a deflection mechanism described below. This RHV is capable of sealing onto the deflection mechanism to prevent fluid leakage and may be part of a duostat modified to comprise a single RHV and two sideports. Other configurations, of course, are possible.

Shaft 202 of balloon catheter 200 is of a sufficient size so that it may readily pass through the lumen 104 of sheath 100. Ideally, we prefer the outer diameter of shaft 202 to be between approximately 0.050 inch and 0.100 inch. More preferably, it is between 0.060 inch and 0.080 inch, and most preferably is about 0.074 inch.

The diameter of inner lumen 208 preferably is large enough to allow free passage of contrast media or other material therethrough so that venograms and similar diagnostic procedures may be readily accomplished. It should also be large enough for the passage of a deflection mechanism as discussed below in greater detail. Finally, lumen 208 should allow the free passage of contrast media or other agents therethrough while occupied by a device such as a deflection mechanism. In general, we prefer that inner lumen have a diameter of between 0.030 inch and 0.080 inches, and is preferably about 0.048 inch. Likewise, inflation lumen 209 preferably has a diameter of between about 0.005 inch and 0.020 inch, and preferably is about 0.014 inch.

The balloon catheter shaft 202 preferably comprises PEBAX tubing having a durometer hardness of between about 60D and 80D, preferably about 72D. Preferably, shaft proximal section 206 has a heat shrink tubing disposed on the outer surface thereof. Preferably, this heat shrink tubing is polymeric and is comprised of clear polyolefin or the like. Distal tip 216 is preferably a soft, atraumatic tip made of a relatively flexible polymeric material similar in composition and stiffness to distal tip 112 of sheath 100. In one embodiment, distal tip is radiopaque.

The working length of balloon catheter shaft 202, which includes the distal tip 216, distal section 204, and proximal section 206, should be between about 50 cm and 90 cm, although it may be longer or shorter depending upon the application. We especially prefer a working length of approximately 70 cm which can accommodate a distal tip 216 of approximately 0.5 cm, a distal section 204 of approximately 6 cm, and a proximal section 206 of approximately 63.5 cm.

The length of the entire catheter 200 in this embodiment (the working length of shaft 202 and the components disposed proximal of proximal section 206 discussed above) should be about 77.5 cm. In general, we prefer that the balloon catheter shaft 202 be between about 15 cm and 20 cm longer than sheath 100.

Of course, the absolute and relative lengths of each component of catheter 200 may vary considerably. The particular application in which catheter 200 and the entire system of the present invention is to be used will dictate the particular dimensions and materials for its various components (as well as each of the components of the inventive system) described herein.

Occlusion balloon 211, when inflated, should have a diameter sufficient to seal the coronary sinus ostium. This inflated diameter will typically be between about 0.2 inch and 1.0 inches, and more preferably, between about 0.4 inch and 0.8 inches. We prefer balloon 211 to comprise an inelastic or elastic polymeric material. Polyurethane (e.g. PELLETHANE 80A durometer, World Medical, Inc., Miami Fla.) is especially preferable. The inner diameter of the uninflated balloon 211 typically will be between about 0.04 inch and 0.08 inches, and more preferably between about 0.056 inch and 0.070 inches. The balloon wall thickness typically will be between about 0.002 inch and 0.006 inches, and more preferably about 0.004 inches. Finally, the balloon 211 length typically will be between about 6 mm and 14 mm, and more preferably between about 8 mm and 12 mm.

Deflection Mechanisms and Micro-Deflection Mechanism

The deflection mechanism and the micro-deflection mechanism are two separate components of the present invention. Deflection mechanism 300 is designed for use in the balloon catheter 200, and is similar in many respects to the micro-deflection mechanism 400, only larger. Micro-deflection mechanism 400 is designed for use in a variety of applications where precise control and deflection of a device such as a lead, electrophysiology catheter, or other similar IMDs, is needed. Its small size relative to deflection mechanism 300 renders it useful in a wide range of applications in which its small size and flexibility may be relied upon.

FIG. 3 is a plan view illustrating components of both the deflection and micro-deflection mechanisms, although it will be described in terms of the deflection mechanism 300 for discussion purposes. Deflection mechanism 300 generally comprises a proximal section 304, a distal section 306, and a distal tip 308. Adjacent the proximal section 304 is handle 310, a preferred variation of which is shown in detail in FIGS. 4A and 4B.

Deflection mechanism 300 is designed to be place through proximal port 218 of the balloon catheter 200 and into the inner lumen 208 such that the deflection mechanism distal tip 308 generally reaches distal section 204, and preferably distal tip 216, of balloon catheter shaft 202. When the handle 310 is activated, the distal section 306 of deflection mechanism 300 deflects in a predetermined fashion, thus deflecting the distal section 204 of the balloon catheter in a similar fashion. In this way, balloon catheter 200 (or any device into which deflection mechanism 300 is disposed) may be torqued to conform to the particular lumen or cavity into which it is disposed.

Shaft 302 of deflection mechanism 300 comprises a tubular member such as hypotube 312, preferably made of metallic biocompatible material such as medical grade stainless steel, titanium, nitinol, alloys of these, or any suitable material as known to those of skill in the art. Hypotube 312 preferably has an outside diameter small enough to fit within inner lumen 208 of catheter 200 and is preferably less than 0.048 inch. As shown in FIG. 3, hypotube 312 is beveled to form a strain relief 316 at the distal end of hypotube 312. Of course, this particular configuration of hypotube 312, as well as other aspects of the FIG. 3 deflection mechanism 300, is merely exemplary. Other configurations that serve the purposes of this invention are within the scope of this disclosure as well.

Disposed within a central lumen of hypotube 312 is a pull wire 320, which can be a stainless steel, titanium, nitinol or other metal or alloy or even polymeric wire which when pulled activates the deflection of distal section 306 of deflection mechanism 300. Pull wire 320 is attached to a flat spring 322, which is disposed in the distal section 306 of deflection mechanism 300. Spring 322 is attached to hypotube 312 using any suitable attachment method, such as welding, brazing, soldering, adhesives, or the like as is known to those of skill in the art. Spring 322 may be brazed to hypotube 312 along braze zone 314 as seen in FIG. 3. Likewise, any similar suitable attachment techniques may be used to attach pull wire 320 to spring 322. In one embodiment, the pull wire and spring are brazed to one another in braze zone 318 as seen in FIG. 3.

Distal deflection region 306 is preferably covered with compliant polymeric medical grade tubing, such as polyester, PEBAX, and tetrafluoroethylene. Especially preferred is a polymer of tetrafluoroethylene hexafluoropropylene and vinylidene fluoride known by its acronym as THV. This prevents fluid intrusion into the deflection mechanism.

In an especially useful variation of the invention in which the system is used for implanting a lead, the balloon deflection mechanism 300 will be of sufficient diameter to provide rigidity to the balloon catheter 200 during introduction into the coronary sinus ostium. The curve reach and deflection range should be sufficient to provide easy introduction into the coronary sinus ostium, and the entire assembly should provide adequate pull strength to deflect and torque the distal portion 204 of balloon catheter shaft 202 during manipulation into the coronary sinus ostium.

Figure 4B:
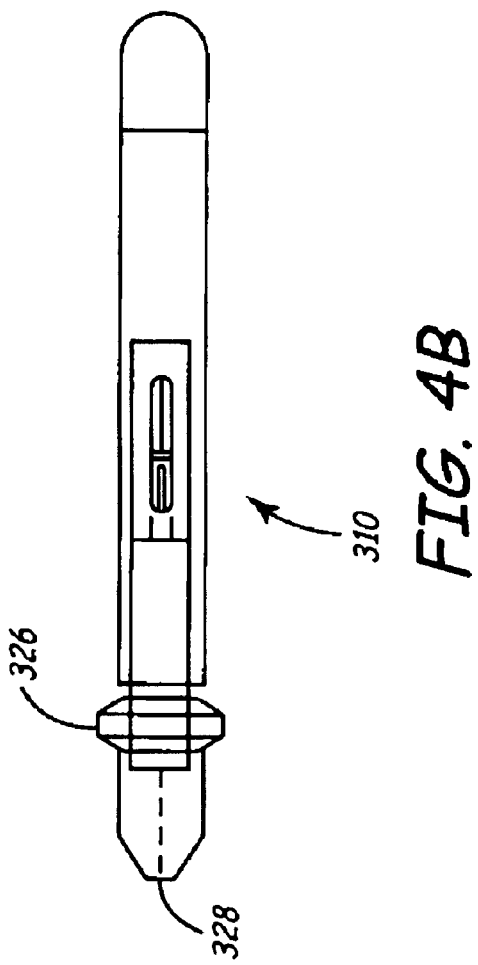
FIGS. 4A–4B are various views of a deflection mechanism handle of the present invention.
Figure 4A:
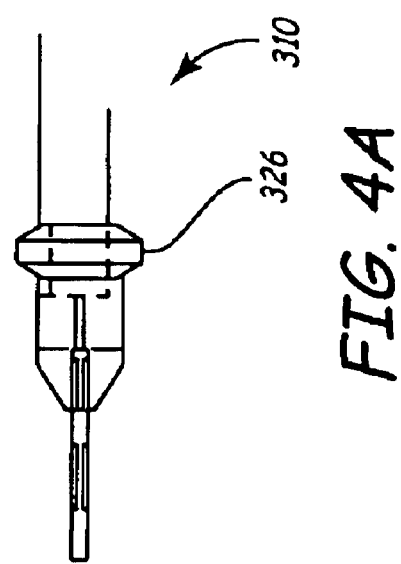

Turning now to FIGS. 4A–4B, a useful variation of handle 310 for manipulating deflection mechanism 300 is shown. Handle 310 includes body 324 and activation mechanism 326. Activation mechanism 326 may be manipulated by pushing distally or pulling proximally along a longitudinal axis of handle 310. The machined parts of these components may be polymeric. For example, a thermoplastic such as the acetyl homopolymer DELRIN (E.I. du Pont de Nemours and Company, Wilmington, Del.) may be used for this purpose. The molded parts may be formed of polymeric materials such as ABS (acrylonitrile butadiene styrene) or the like. A proximal end of pull wire 320 is disposed in a central lumen 328 of handle 310 and affixed into handle by means known to those of skill in the art.

Handle 310 is preferably lightweight and ergonomically configured for simple, one-handed operation. The deflection range (the maximum angular displacement the distal tip 308 undergoes when displaced from a straight and undeflected zero-degree position) may be between about 90 degrees and 180 degrees, preferably between about 100 degrees and 135 degrees. Further details of the features and versatility of distal section 306 will be described in greater detail below, as well a detailed description of how deflection is achieved.

Figure 5:
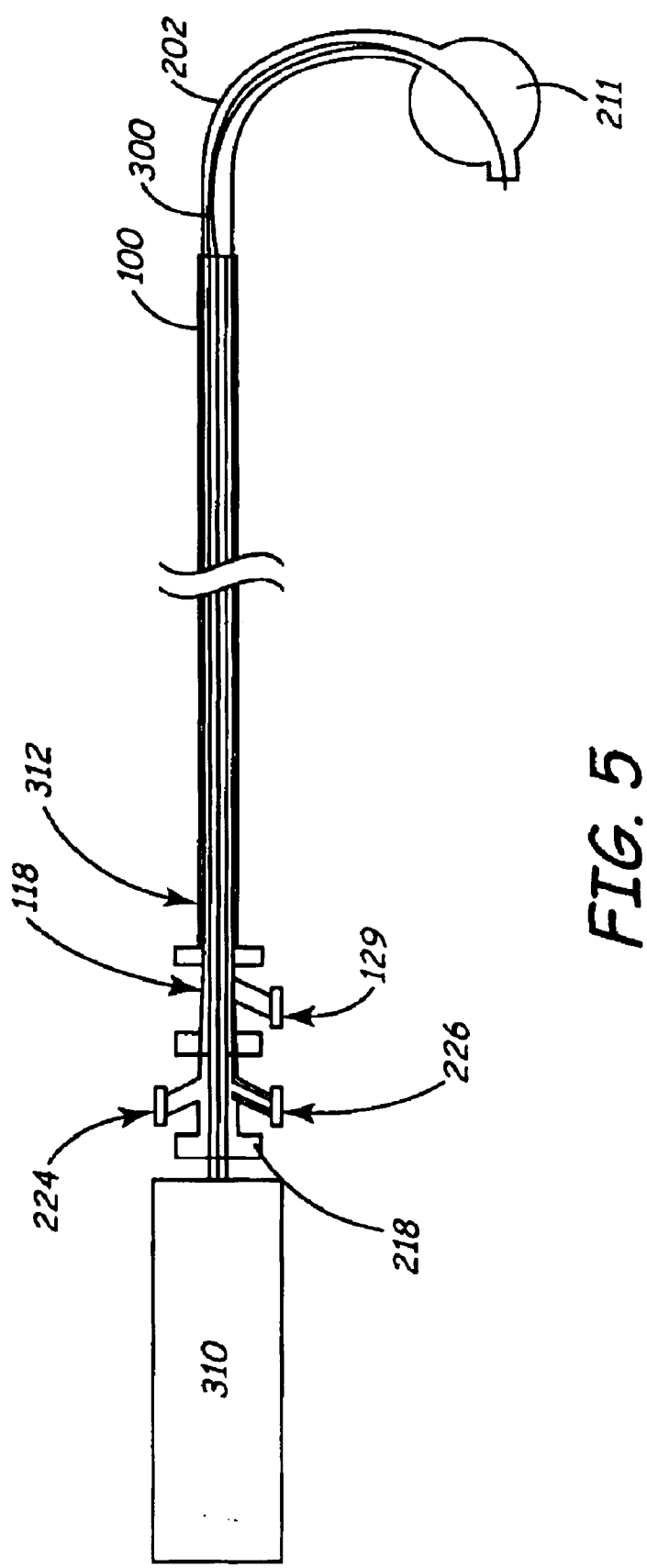
FIG. 5 is a cross-sectional side view of three components of the present invention: a deflection mechanism, an outer sheath, and a balloon catheter with an inflated distal balloon and a deflected distal end.

FIG. 5 depicts three components of the inventive system described above in a partial cross-section. Deflection mechanism 300 with handle 310 is shown disposed in the inner lumen of balloon catheter shaft 202 via the proximal port 218 as previously described. In turn, the combination deflection mechanism 300 and balloon catheter 200 are disposed in the lumen 104 of sheath 100. In FIG. 5, the distal section of balloon catheter shaft 202 is shown in a deflected state via the action of the hypotube/pull wire mechanism. Notice also that distal balloon 211 is inflated with fluid provided through balloon fluid port 224. An RHV 118 for outer peel-away sheath 100 as discussed herein is seen as a flush port 130 disposed on RHV 118. For purpose of clarity, sheath hub 114 is not shown.

In general, there is no limit to the size of the deflection mechanisms described herein. All of the related components are readily scalable to larger or smaller sizes than those disclosed here as would be apparent to one of ordinary skill in the art and as the particular application demands.

Turning now to a more specific discussion of micro-deflection mechanism 400 depicted generally in FIG. 3, the features of this element are largely similar to those of deflection mechanism 300. The features are generally smaller so that they may be used within devices such as leads, electrophysiology catheters, and the like as will be described below.

The micro-deflection mechanism utilizes a hypotube configuration as shown in FIGS. 7A, 7B, and 8A through 8E. We prefer the outer diameter of the micro-deflection mechanism hypotube (not shown) to be between about 0.012 inch and 0.030 inch; preferably between about 0.014 inch and 0.026 inch; most preferably about 0.015 inch. This will allow introduction of the hypotube into a conventional IS-1 lead connector, as well as allow for movement of the hypotube within the entire length of the central lumen of a lead body without causing any undue stress or damage to any of the lead or catheter components.

We also prefer that the micro-deflection mechanism 400 pull wire, which is also preferably stainless steel or nitinol, have an outer diameter of between 0.005 and 0.015 inches, and more preferably between about 0.006 and 0.010 inches. Most preferably, the outer diameter is about 0.008 inch.

During deflection, we prefer that the distal-most 10 mm to 30 mm of the assembly 400 deflect, which in a preferred application, will allow the lead into which assembly 400 is placed to engage the coronary sinus ostium. Due to the smaller size and greater maneuverability, assembly 400 may deflect through angles as high 360 degrees and even 450 degrees or more. Such a high angular deflection capability allows the mechanism 400 (and the device into which it may be deployed) to create a tight loop. These high-angle deflections are especially useful in electrophysiology applications in which the micro-deflection mechanism 400 may be deployed in a mapping/ablation microcatheter to effect circumferential ablation patterns and the like in areas such as the cardiac pulmonary vein.

FIGS. 6A–6D depict various components of an especially useful variation of micro-deflection mechanism 400 handle 414. As shown in FIG. 6A, handle 414 includes a body 416 and an activation mechanism 418 that may be manipulated by pushing distally or pulling proximally axially along a longitudinal axis of handle 310. The handle has a relatively small preferred length that may be in the range of 2 inches. This scales well with the other, smaller components of micro-deflection mechanism 400, and also allows for simple, one-hand fingertip operation by a physician. Of course, the sizes may be sized as needed in a manner discussed above.

Micro-deflection mechanism 400 can be used to replace the fixed-curve stylet generally used to provide a deflectable lead or catheter. This deflectable lead or catheter may be more precisely placed in the targeted region of the cardiac venous system, overcoming the problems of state-of-the-art systems. In addition, the micro-deflection mechanism may be used in conjunction with the other components of the inventive system describe herein for deflectable electrophysiological catheters.

Turning now to features that are common to both the deflection mechanism 300 and micro-deflection mechanism 400 (hereinafter referred to in this generic discussion as simply "deflection mechanism"), each operates on the same principal based on a hypotube/pull wire assembly. The pull wire runs through the middle of the hypotube and is attached, via brazing or the like, at the distal end of the deflection mechanism.

The hypotube is allowed to deflect in a predetermined pattern by a series of slots, or kerfs, cut into the hypotube distal section. U.S. Pat. No. 5,507,725 to Savage et al, U.S. Pat. Nos. 5,921,924 and 5,441,483 both to Avitall, U.S. Pat. No. 4,911,148 to Snowski et al, U.S. Pat. No. 5,304,131 to Paskar, the entirety of each which are hereby incorporated by reference, describe various medical devices in which some type of notch is used to effect deflection FIGS. 7 and 8 depict two variations of notch patterns that are useful in the present invention. Because of the scalability of these features, they are useful in both the deflection assembly 300 as well as micro-deflection assembly 400.

In reference to FIGS. 7 and 8, and the following discussion, note that due to the drawing space constraints, the "proximal section" of the hypotube refers to a portion of the deflection mechanism that is proximal only in that it is disposed proximal to the corresponding distal section. It is possible that a considerable length of the hypotubes depicted in FIGS. 7 and 8 exists proximal to the so-marked "proximal section".

In FIGS. 7A and 7B, two hypotube/pull wire combinations are shown in top and side views, starting from the top of the page, respectively. FIG. 7A depicts an assembly 700 in which a pull wire 704 is brazed, soldered, or otherwise affixed to the distal end of hypotube 702 at hypotube distal section 708. Note that pull wire 704 is deployed inside hypotube 702. The pull wire is disposed in the interior of hypotube 702 all the way to the hypotube distal section 708 where it is affixed to hypotube 702 as described above. In general, pull wire 704 is affixed in handle 310 such that when the handle is activated, hypotube distal section 708 will deflect on the same side on which notches 710 (or as discussed below, the reduced wall thickness of hypotube) are located.

Each notch or kerf 710 is progressively deeper as one moves from the proximal end 706 of hypotube 702 to the distal end 708. This particular feature will cause the hypotube to deflect in a smooth consistent curve. Note that the spacing between notches 710 is constant, and the only dimension of each notch 710 that changes its depth. The width remains constant. Each of these parameters may vary as performance requires.

Further, the centroids of each notch are aligned along a single, straight liner longitudinal axis as one moves from proximal section 706 to distal section 708. This axis along which the notches are aligned may be nonlinear. For instance, the axis may be sinusoidal to effect a serpentine deflection profile, with a constant or varying pitch, or the axis may have some other curvilinear or even stepwise shape. Regardless of whether the notch centroids are aligned along a linear or nonlinear axis, the centroid of each notch does not have to line up along such an axis.

Note also that the distance between adjacent notches as one moves from one end of a notch to the other end of hypotube of FIG. 7A remains constant. That is, the longitudinal axes of the notches are parallel to one another. This aspect of the notches or kerfs may also change depending upon the application.

Another variable that may affect the shape and performance characteristics of the assembly 700 is the depth to which the notches 710 are cut into the hypotube. For instance, in the assemblies of FIGS. 7A and 7B, the notches are cut completely through the wall thickness of hypotube 702. This need not be the case. It is within the scope of the invention to provide notches in hypotube 702 in which a discrete amount of material is removed from the hypotube without penetrating through the hypotube thickness. A wide variety of depth profiles and patterns in etching each notch is therefore envisioned.

Taking this concept one step further, hypotube 702 need not contain a series of notches or kerfs to achieve the desired preferential distance deflection shape and response. For instance, it is within the scope of the invention to preferentially machine or etch the bulk of hypotube 702 in an asymmetric fashion so that when the pull wire 704 is activated, the distal section 708 of hypotube 702 deflects in a predetermined pattern. In other words, the wall thickness of hypotube 702 can be made to vary a function of length and/or circumferential position in patterns ranging from a simple tapering pattern to complex patterns in which correspondingly intricate and complex deflection shapes and resources may be had. Such a concept can be used alone or in conjunction with the use of notches or kerfs as described herein.

Each of the parameters described above, as well as other parameters such as hypotube wall thickness, material selection, etc. may be chosen to effect a particular deflection pattern and response depending upon the application for which the hypotube/pull wire assembly (such as assembly 700) is intended. Furthermore, variations in many of these parameters from notch-to-notch may also be made. For instance, one notch may have a rectangular profile, while another notch on the same hypotube may have a circular profile, etc.

Software may be utilized to aid the designer, by way of mathematical algorithms and the like, to ascertain the optimal profile for hypotube 702 given a desired deflection shape, etc. For instance, a designer may be able to choose the application for which the assembly is to be used, and the software may select a number of alternative shapes from which the designer may choose. Once a deflection shape is chosen, the software will then calculate the optimal hypotube profile.

FIG. 7B shows an assembly 750 in which hypotube 752 and pull wire 754 are arranged in a similar fashion to those described above and shown in FIG. 7A. The only difference in the assembly of FIG. 7B is that the constant spacing between the notches 756 is larger than that in the assembly of FIG. 7A. This increased but constant spacing between notches 756 results in hypotube 752 being slightly heavier, since less material has been cut away from the hypotube. When assembly 750 is deflected, this means that distal section 760 will deflect through a smaller angle with a larger curve diameter (although the deflection shape will generally be similar as that of the deflected assembly 700 due to the similar size, shape, and orientation of the notches in each assembly) than that experienced by assembly 700 in FIG. 7A for a given deflection force.

Figure 8C:
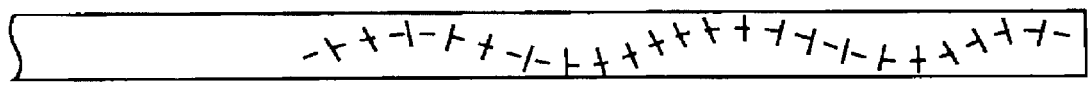

Turning now to FIGS. 8A through 8E, additional variations of a notch pattern are shown (the pull wire is omitted for clarity). In FIG. 8A, hypotube 810 with proximal section 812 and distal section 814 contains a series of linear notches 816 similar to those of FIGS. 7A and 7B, except that each end of notches 816 contain a secondary notch 818 oriented generally perpendicular to notch 816. This notch design causes the distal section 814 of hypotube 810 to deflect in a similar fashion as described above, possibly with a tighter curve diameter.

The hypotube of FIG. 8B is identical to that of FIG. 8A, except that the notch pattern begins closer to the proximal section 822 of hypotube 820. A longer length of hypotube distal section 824 will therefore deflect when activated by the pull wire.

FIG. 8C is a plan view depicting an embodiment of deflection mechanism wherein the notches are arranged in a non-linear manner. For example, a sinusoidal pattern is depicted, although many other types of patterns are possible.

Figure 8D:
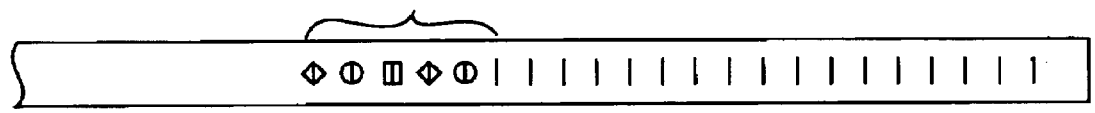

FIG. 8D is a plan view depicting an embodiment of deflection mechanism wherein the notches are of different shapes and sizes. For example, the notches may be circular, triangular, rectangular, or any other pattern desired to allow the deflection mechanism to assume a desired shape when tension is applied to the pull wire. The notches may all have a uniform shape and size, or alternatively, may have different shapes and/or sizes.

Figure 8E:
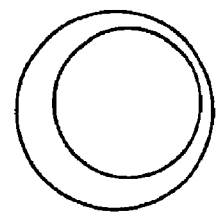
FIG. 8E is a cross-sectional view of a deflection and micro-deflection mechanism having a tubular member with an irregular wall thickness to provide a preferred bending direction.

FIG. 8E is a cross-sectional view depicting an embodiment of the deflection member wherein the hypotube has walls that are not of a consistent thickness. The thinner region of the wall defines a preferred bending direction when tension is applied to the pull wire. In one embodiment, both a thinner wall thickness and the creation of notches in the thinner region may be used to provide the deflection mechanism in the hypotube or other tubular member.

The notches or kerfs described herein and shown in the figures, as well as the varying wall thickness of the hypotube, may be created by any means know to those of skill in the art. They may be machines by traditional, laser, electron-discharge, or similar machining methods, they may be chemically etched, etched using known photolithographic techniques, etc.

A particularly useful feature in the deflection mechanisms described herein is the active control feature of the deflection mechanism handle (both handle 310 as well as handle 414). Once the handle activation mechanism is engaged to deflect the distal section as described above, the deflection can be reversed only by the positive input of a user to disengage the same activation mechanism. In one embodiment of the deflection mechanism described above and shown in FIGS. 4A–4B and FIGS. 6A–6D, release of the activation mechanisms 326 and 418 after these mechanism are deployed results in the distal section remaining in a deflected position. Reversal of this deflection requires that the physician-user retract the activation mechanism, whereupon the distal section 306 will resume the undeflected state until the handle is activated once again. This feature allows the physician-user to manipulate other portions of the inventive system or to perform other tasks while the distal section 204 of balloon catheter 200, for example, remains in the intended deflected or undeflected state. Of course, it is within the scope of the invention to design the handle so that activation to deflect distal section is automatically reversed to return the distal portion to a default undeflected state. This may be accomplished by a bias spring or equivalent mechanism that activates when the physician releases the positive input causing the initial deflection. Such a design may also bias the distal end of the deflection mechanism to automatically reverse to a default deflected position.

Another feature common to both handles 310 and 414 is the presence of one or more limit stops that may be built into the handle. These limit stops are designed to prevent over-deflection of the deflection mechanism.

Deployment of Cardiac Lead

Figure 9:
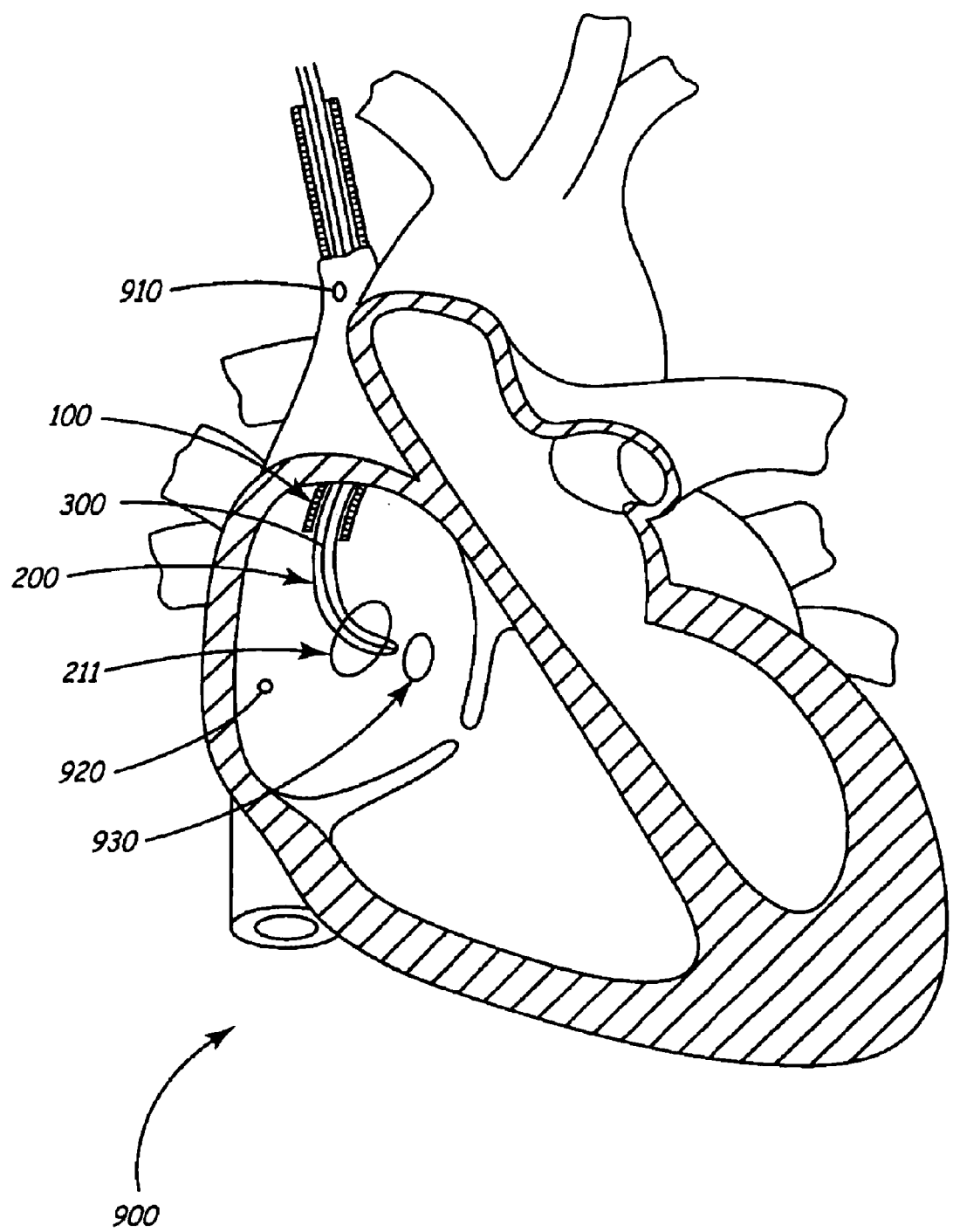
FIGS. 9–11 depict a method for accurately placing an endocardial lead into the cardiac venous system through the coronary sinus ostium using a system of the present invention.
Figure 10:
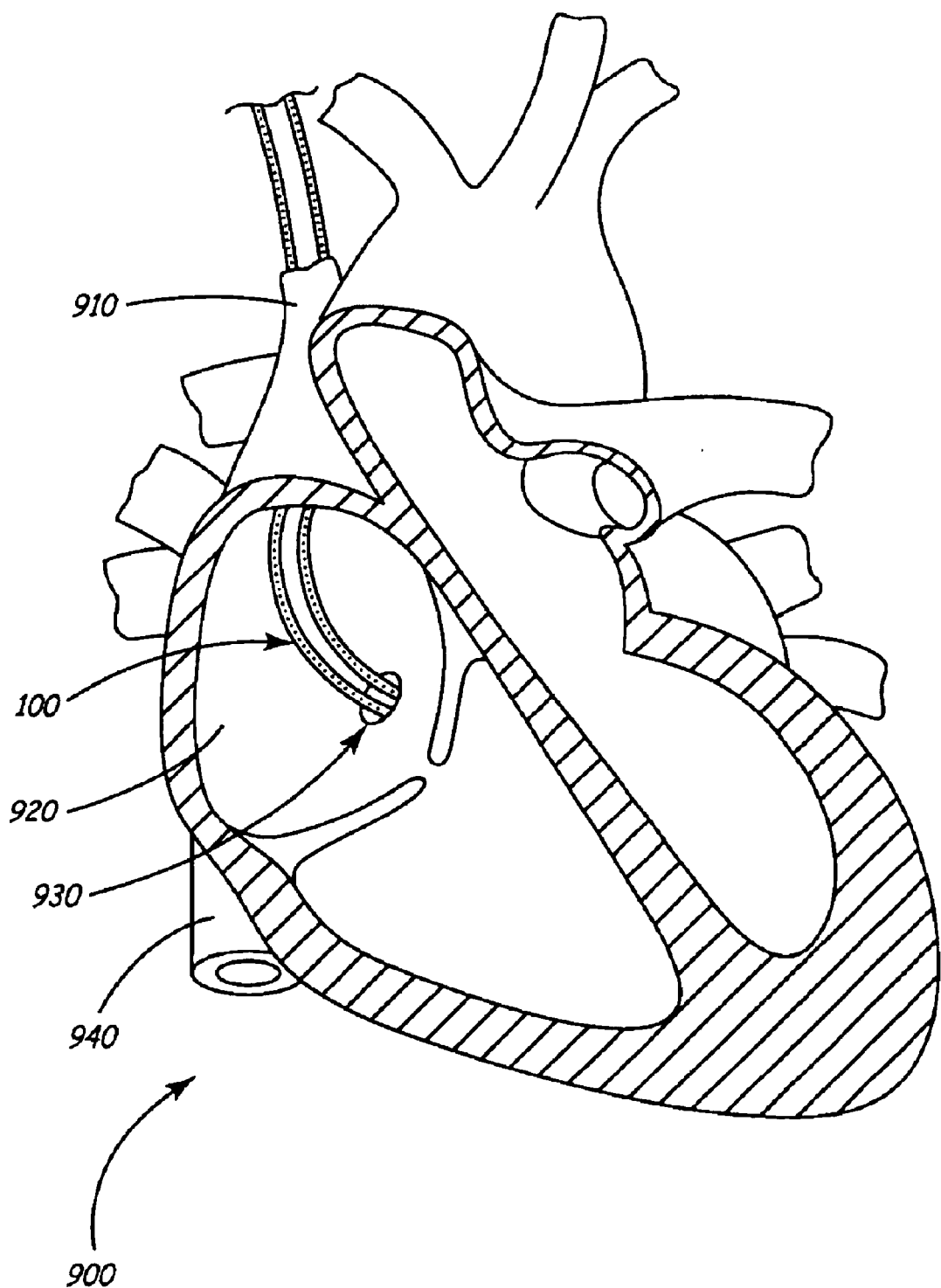
Figure 11:
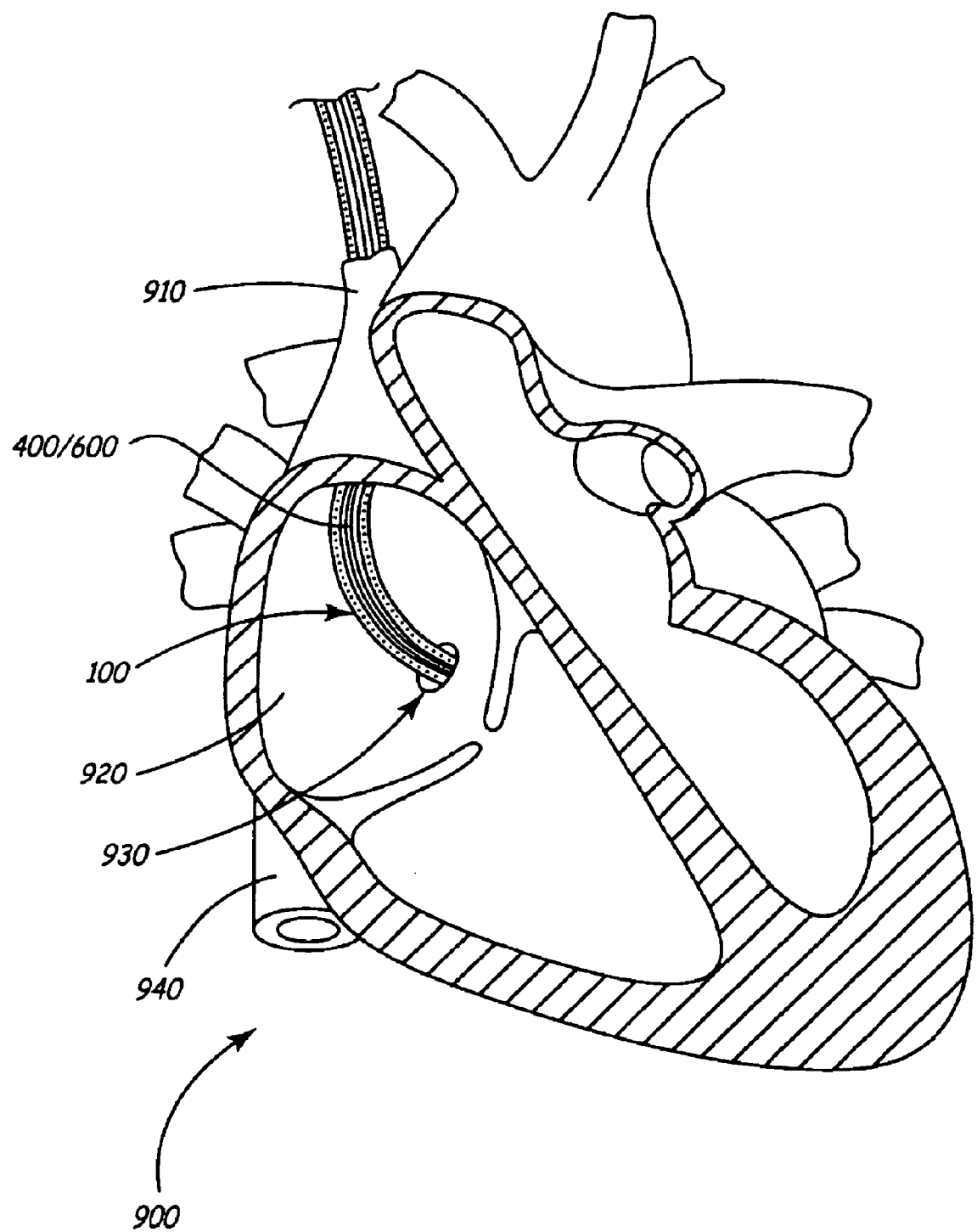

Turning now to FIGS. 9–11, a particularly useful application for the system herein described is shown and is discussed below. In particular, a method for intravascularly deploying the system into the coronary sinus, obtaining an occlusive venogram, and accurately subselecting a venous branch and placing a cardiac lead therein is described.

To prepare for the procedure, balloon catheter 200 is inserted within the lumen 104 of outer sheath 100 to create a sheath/catheter combination. A deflection mechanism 300 is advanced into the large lumen 208 of the balloon catheter via proximal port 218 so that the distal tip 308 of the deflection mechanism shaft 308 is generally disposed in balloon catheter shaft 202 near shaft distal tip 216 as previously describe. This creates a combination sheath/catheter/deflection mechanism system as shown in FIG. 5. Typically, a portion of shaft 202 will extend out through and beyond the lumen 104 at the sheath 100 distal end 112 for some length.

This three-component system is introduced into the patient's venous system through the cephalic, subclavian or femoral vein via a conventional introducer as known to those of skill in the art. The physician uses the introducer to dilate the selected vein and then advance the system through the introducer into the selected vein.

Typically under fluoroscopic guidance, the physician navigates the three-component system through the vasculature to and through the superior vena cava 910 or inferior vena cava 940 (see FIG. 9) and into the heart 900 right atrium 920. At this point, the distal tip 216 of shaft 202 and distal balloon 211 engage the coronary sinus ostium. The deflection mechanism is used to help steer the shaft 202 distal tip 216 into place. Balloon 211 is then inflated, and contrast is injected into the coronary veins through the distal port 214 of shaft 202. This creates an occlusive venogram for visualizing the coronary veins in advance of placing the lead in the desired location.

Next, while balloon 211 is still in the coronary sinus, the outer sheath 100 is advanced into the coronary sinus over the catheter shaft 202 so that it may be available as a conduit for lead placement. Once the sheath 100 is in place, the balloon 211 is deflated and the balloon catheter 200 and the associated deflection mechanism 300 are proximally withdrawn from sheath 100, leaving sheath 100 alone in place in the coronary sinus as shown in FIG. 10.

Next, the micro-deflection mechanism 400 is placed into a central lumen of a lead 600 so that the deflectable distal section of micro-deflection mechanism 400 generally engages the distal section of the lead 600. The combination of these components is then advanced into the lumen 104 of sheath 100 and into the coronary sinus ostium as seen in FIG. 11. From here, the physician will activate the deflection mechanism to steer the lead/micro-deflection mechanism combination. In one embodiment, the micro-deflection mechanism may be used to subselect a venous branch into which the lead is to be permanently placed. Of course, the particular deflection shape and characteristics of micro-deflection mechanism have been selected by the physician for optimal use in navigating the venous system and creating the shape for the lead to assume during lead placement.

Once the lead 600 is placed and the pacing thresholds are acceptable, the RHV 118 is removed from the sheath and slid over the lead connector (alternatively, RHV 118 may be split). Next, preferably with the aid of a special slitting tool such as a customized razor blade attached to the sheath 100, the sheath 100 and hub 114 are split along score 126 as the sheath is pulled away from the lead 600 and removed from the body.

Micro-deflection mechanism 400 may be withdrawn from the lead 600, after which the lead 600 is the only component left in the body. Lead 600 remains in place, and may be coupled to a pulse generator, cardioverter/defibrillator, drug delivery device, or another type of IMD.

As discussed throughout the specification, the method outlined above is merely exemplary of one way to deploy a cardiac lead according to the present invention. Many alternative applications for the invention are possible. Significant variations from this technique may occur within the scope of the present invention.

For example, in one embodiment, the deflection mechanism that is adapted to be inserted within the balloon catheter is a steerable catheter such as an electrophysiology (EP) catheter. One example of a catheter having a suitable steering mechanism is the Marinr catheter commercially available from Medtronic Corporation.

FIG. 12 is a plan view of a steerable catheter that may be used to navigate the balloon catheter 200 into the coronary sinus. The catheter 1000 is an anatomically-conforming, dual curve EP catheter used to sense electrical signals in the heart and associated vasculature. The catheter includes a shaft 1004 having an atraumatic distal end 1006 and a proximal end 1008. Shaft 1004 may have an outside diameter of less than approximately 0.06 inches and a length of about 50 mm to 110 mm. Proximal end 1008 is mounted to a handle 1010 having axially slidable manipulator rings 1012 and 1013, and a rotatable lateral deflection ring 1014 operably connected to proximal and distal manipulator wires carried by the body of the catheter. Sliding manipulator rings 1012 and 1013 cause a deflectable tip 1020 of catheter shaft 1004 to deflect as shown in FIGS. 12A and 12B between, for example, the solid-line and dashed-line positions of FIG. 12B. Rotating ring 1014 causes lateral deflection of tip 1020 through the torquing action of a core wire as shown in FIGS. 12C.

A steerable EP catheter of the type shown in FIGS. 12 through 12C is adapted to be inserted within the inner lumen of the balloon catheter, which in turn, is inserted within the lumen 104 of the outer sheath 100 to create an alternative sheath/catheter combination. As previously described, this assembly may be advanced into the chambers of the heart. Next, the EP catheter distal tip may be advanced beyond the distal end of the outer sheath to guide the balloon catheter into the coronary sinus. The range of motion provided by the steerable catheter as noted above makes it particularly suitable for cannulating the coronary sinus and utilizing the balloon catheter to obtain a venogram in the manner discussed above. Then the balloon catheter and the steerable catheter are removed from the sheath so that the sheath may be used to place an IMD with a microdeflection mechanism in the manner discussed above.

According to another aspect of the invention, the system described herein may be used for deploying a wide array of devices in the coronary venous structure, the pulmonary venous structure, or any organ with large enough vessels for the introduction of the system. In addition, the system can be used in extravascular applications such as in the deployment of cochlear implants, in body cavities, muscle tissue, and the like.

The balloon catheter 200 can be used for the introduction of drugs or other media or agents within a very discrete region of a vessel. Note that the balloon on the balloon catheter 200 described herein is optional. The deflectable catheter may be used without a balloon, for improved access and maneuverability.

With respect to the micro-deflection mechanism 400, due to its ability to be scaled to a very small size, it may be used for interventions into the spinal column, tiny vessels in the brain, liver, kidney, or any other suitable organ. In addition, sensor such as electrodes for recording signals and possibly ablating tissue may be incorporated into the micro-deflection mechanism 400. Fiber optics for the introduction of light for visualization or optical recording or sensing may be incorporated into either deflection mechanism.

The deflection mechanism may also be used to deliver drugs or other therapeutic or diagnostic agents or materials as described above.

The intralumenal visualization system of the present invention may alternatively be defined in terms of a navigation pathway tool kit. The tool kit provides the operator with a choice of tools to select an approach for the delivery of a medical electrical lead that is best suited for the patient receiving the lead. The navigation pathway is defined as the combination of the delivery sheath, positioned to provide access to the coronary sinus, and the venogram that serves as a map of the coronary veins. The present invention also includes additional lead accessory tools, with unique features, to facilitate both lead delivery and stable lead implant while the delivery sheath is being removed.

Navigation Pathway Tool Kit

FIG. 13 is a schematic diagram of a tool kit used to establish venous access in a system for delivering medical devices within a coronary venous system according to the present invention. According to the present invention, a tool kit 10 for establishing venous access includes a percutaneous introducer kit 5, used to gain venous access via the known Seldinger technique, and including a needle 1, a syringe 3, an introducer guide wire 4, an introducer sheath 7, an introducer dilator 9, and an introducer slitter 11.

According to the present invention tool kit 10 also includes at least two different types of delivery sheaths, such as a right-sided venous access delivery sheath 21 and a left-sided venous access delivery sheath 23, a delivery sheath dilator 22, a guide wire clip 6, and a delivery sheath slitter 24. Delivery sheath 21, which has a length of approximately 40 cm, extends from a proximal portion 14 to a distal portion 12 formed into a curvature suited for an approach to the coronary sinus from a right-sided venous access point, while delivery sheath 23, which has a length of approximately 45 cm, extends from a proximal portion to a distal portion 13 formed into a curvature suited for an approach to coronary sinus from a left-sided venous access point. The general construction of such delivery sheaths is described above in conjunction with FIGS. 1A and 1B.

Delivery sheath dilator 22 is inserted within a lumen 37 at proximal portion 14 of delivery sheath 21, 23 in order to stiffen and straighten distal portion 12, 13 for insertion of delivery sheath 21,23 into a venous system after access has been gained using percutaneous introducer kit 5.

Dilator 22 has a central lumen that extends along the entire length of dilator 22, is open at both ends, and is of sufficient diameter to slide over introducer guide wire 4 once introducer guide wire 4 is inserted within the central lumen of dilator 22. Introducer guide wire 4, which is approximately 0.035" in diameter and has a j-shaped tip 18, is sufficiently long, at minimum approximately 100 cm, in order to cannulate the coronary sinus.

Following introduction of guide wire 4 within the coronary vein using the Seldinger technique, and once dilator 22 is inserted within delivery sheath 21 or 23 and delivery sheath 21 or 23, with dilator 22 therein, has been inserted over introducer guide wire 4, dilator 22 is removed. A distal tip 15 of delivery sheath 21, 23 is then directed into the coronary sinus. In order to prevent dissection of the coronary sinus when advancing delivery sheath 21 or 23, tip 18 of introducer guide wire 4 is first advanced distally through delivery sheath 21 or 23 and extended outward from distal tip 15 of delivery sheath 21 or 23 and advanced within the coronary vein. Once guide wire 4 is positioned within the coronary vein, delivery sheath 21 or 23 is advanced over guide wire 4 with distal tip 15 being directed over introducer guide wire 4 through the coronary sinus and away from a wall of the coronary sinus.

Figure 14:
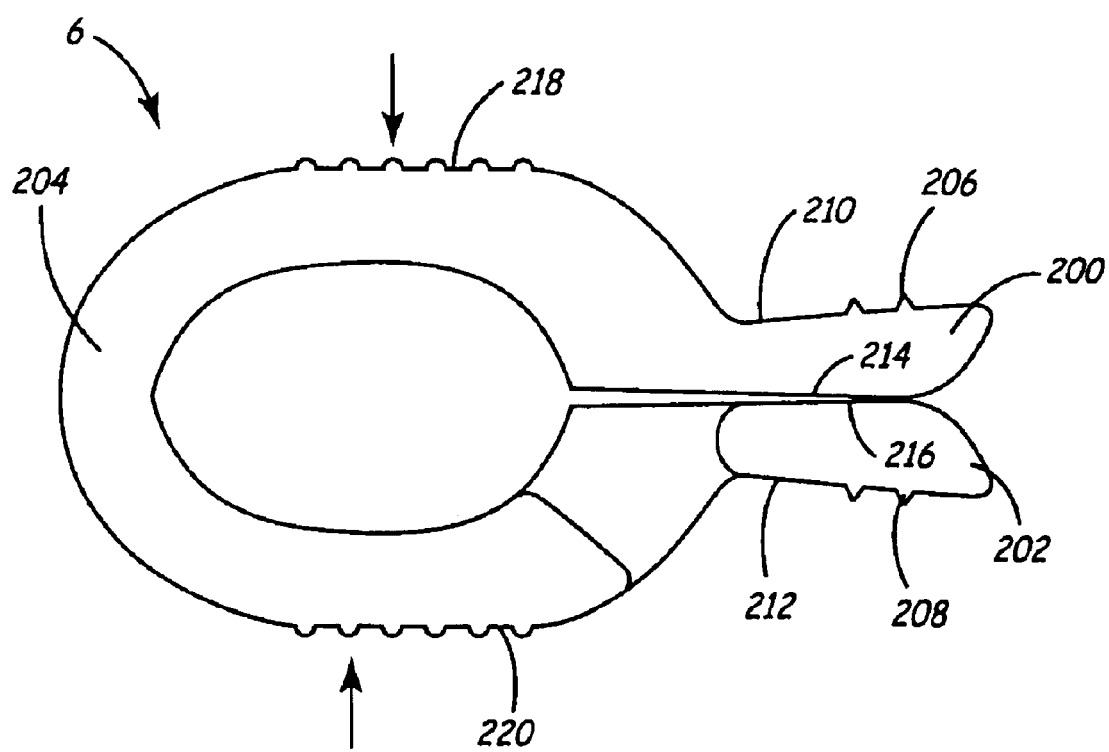
FIG. 14 is a schematic diagram of a guide wire clip of a tool kit according to the present invention.

FIG. 14 is a schematic diagram of a guide wire clip of a tool kit according to the present invention. As illustrated in FIG. 14, according to a preferred embodiment of the present invention, guide wire clip 6, such as product number 35110, commercially available from Qosina Components, includes a first engagement arm 200 and a second engagement arm 202 extending from a compression portion 204. Engagement arms 200 and 202 each include a number of engagement tabs 206 and 208, respectively, positioned along a respective front portion 210 and 212 of engagement arms 200 and 202. When guide wire clip 6 is in a non-engaging open position, as illustrated in FIG. 14, a back portion 214 of engagement arm 200 is engaged against a back portion 216 of engagement arm 202.

Figure 15:
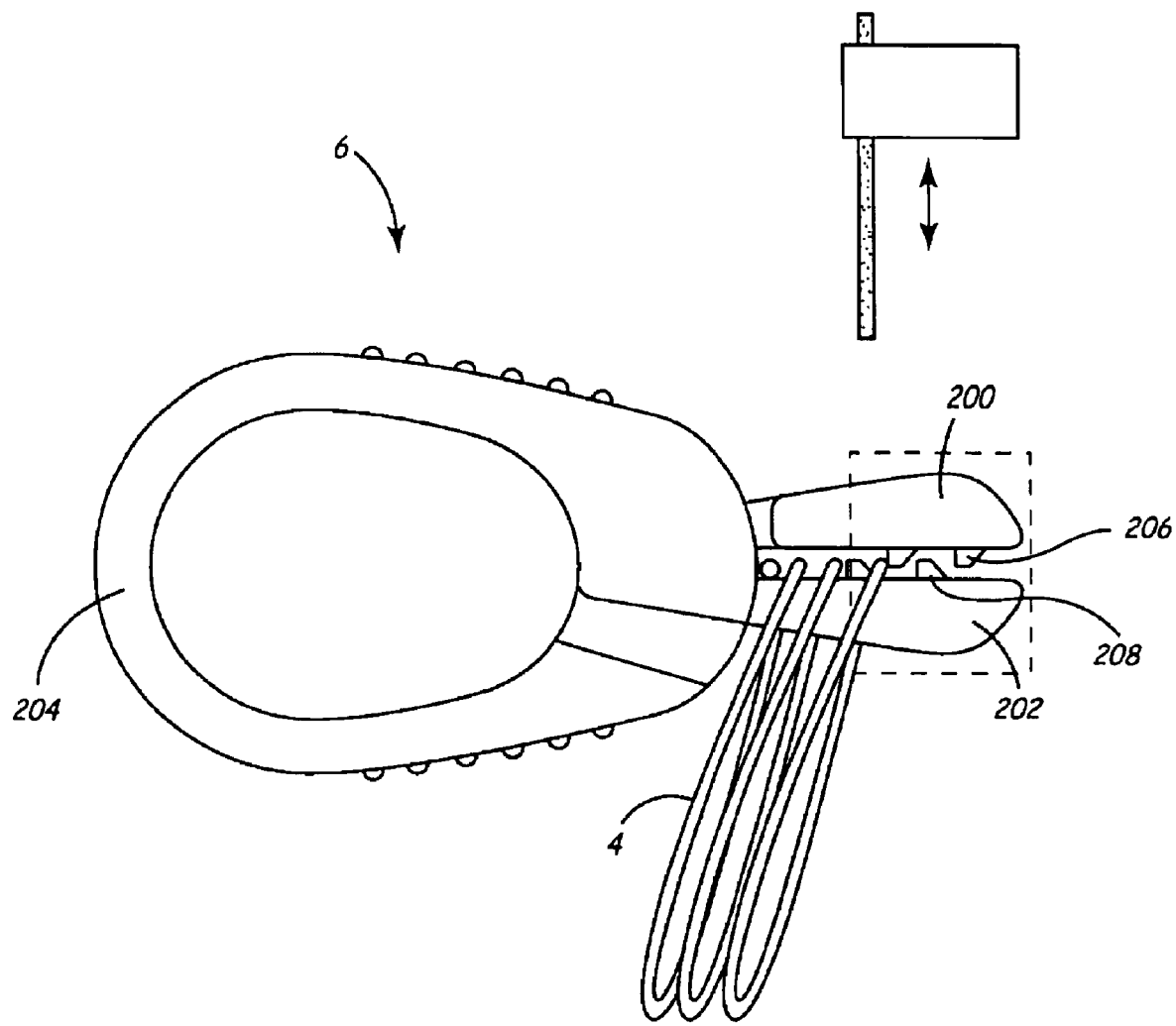
FIG. 15 is a schematic diagram of a wire clip of a tool kit according to the present invention.

FIG. 15 is a schematic diagram of a wire clip of a tool kit according to the present invention. By applying appropriately directed pressure at gripping portions 218 and 220, engagement arms 200 and 202 are re-positioned to grip guide wire 4 between engagement tabs 206 and 208 in an engaging closed position, as illustrated in FIG. 15. As a result, excess length of guide wire 4 can be looped and clipped to surgical drapes, for example, so that guide wire clip 6 secures the excess length of guide wire 4 to prevent the excess length of guide wire 4 from entering the sterile field when guide wire clip 6 is in the closed position. At the same time, while pressure applied by engagement tabs 206 and 208 on guide wire 4 when guide wire clip 6 is in the closed position attaches guide wire 4 to surgical drapes, for example, engagement tabs 206 and 208 minimize the pressure exerted by guide wire clip 6 on guide wire 4 so that guide wire clip 6 does not prevent some movement of guide wire 4 through engagement tabs 206 and 208. In this way, guide wire 4 can be repositioned without having to be removed from guide wire clip 6.

It is understood that although guide wire 4 is shown in FIG. 15 as being looped through engagement tabs 206 and 208, guide wire 4 could also be positioned between engagement tabs 206 and 208 in a non-looped manner. As a result, guide wire clip 6 assists in positioning excess length of guide wire 4, in either a looped or a non-looped manner, to prevent the excess length from entering the sterile field, while allowing guide wire 4 to be re-positioned relative to guide wire clip 6.

According to an alternative embodiment of the present invention, distal portions 12,13 of delivery sheaths 21 and 23 may be straight. A steerable catheter 1002, illustrated in FIGS. 12, and 12A–C, is included in this alternate embodiment of tool kit 10. Steerable catheter 1002, inserted within a lumen of straight delivery sheath imparts selectable curvature to delivery sheath distal segment for directing delivery sheath distal tip 15 to the ostium of the coronary sinus. Steerable catheter 1002 may replace dilator 22 and introducer guide wire 4 as a means for inserting delivery sheath 21, 23 into the venous system and directing distal tip 15 to the coronary sinus.

As illustrated in FIG. 13, tool kit 10 of the present invention also includes a venogram balloon catheter 20. Balloon catheter 20 is delivered to the coronary sinus within lumen of delivery catheter 21, 23 in order to obtain a fluoroscopic map, or venogram, of the coronary venous system. The general construction of balloon catheter 20 and method of use was described above in conjunction with FIGS. 2A–B.

FIG. 16 is a schematic diagram of a rotatable hemostasis valve (RHV) of a tool kit according to the present invention. As illustrated in FIG. 16, according to the present invention, a rotatable hemostasis valve (RHV) 27 of tool kit 10 includes a non-standard Touhy Borst valve 28, a side arm flush port assembly 26, and a non-standard male luer fitting 16 (FIG. 39) within a locking collar 8. Proximal portion 14 of delivery sheath 21, 23 is terminated with a slittable hub 25 of delivery sheath 21 or 23, such as the slittable hub described in U.S. Pat. No. 6,159,198 to Gardeski et al., which is incorporated in its entirety herein. Slittable hub 25 includes non-standard female luer fitting 37 for the connection of RHV 27. RHV 27 is connected to hub 25 prior to inserting delivery sheath 21, 23 into venous system. According to the present invention, non-standard male and female luer fittings 16 and 37 have a diameter approximately twice that of standard luer fittings that are well known in the art. Furthermore, Touhy Borst valve 28 has a larger maximum inner diameter (not shown) than standard Touhy Borst valves also well known in the art. The advantage of larger diameter luer fittings and Touhy Borst valve 28 will be presented, with a more detailed description of RHV 27, below, in conjunction with FIGS. 38 and 39.

Hub 25 has an opening large enough to accommodate a special rotatable hemostatic valve (RHV) 27, to which it is detachably secured by, e.g. an annular ring on the inner diameter of valve 27. A central lumen 33 in RHV 27 is aligned and in fluid communication with the lumen within a shaft 36. Lumen 33 has a diameter large enough to accommodate a balloon catheter and a typical lead connector, such as an IS-1-type connector, for example. An optional side arm 26 may be disposed on RHV 27 in fluid communication with lumen 33. RHV 27 may also be splittable via a scoring or perforation as described above.

An annular polymeric locking collar 8 is disposed on the outside diameter of RHV 27 distal portion proximal to the point where hub 25 meets RHV 27. In this embodiment, rotation of collar 8 locks RHV 27 to hub 25.

Figure 17:
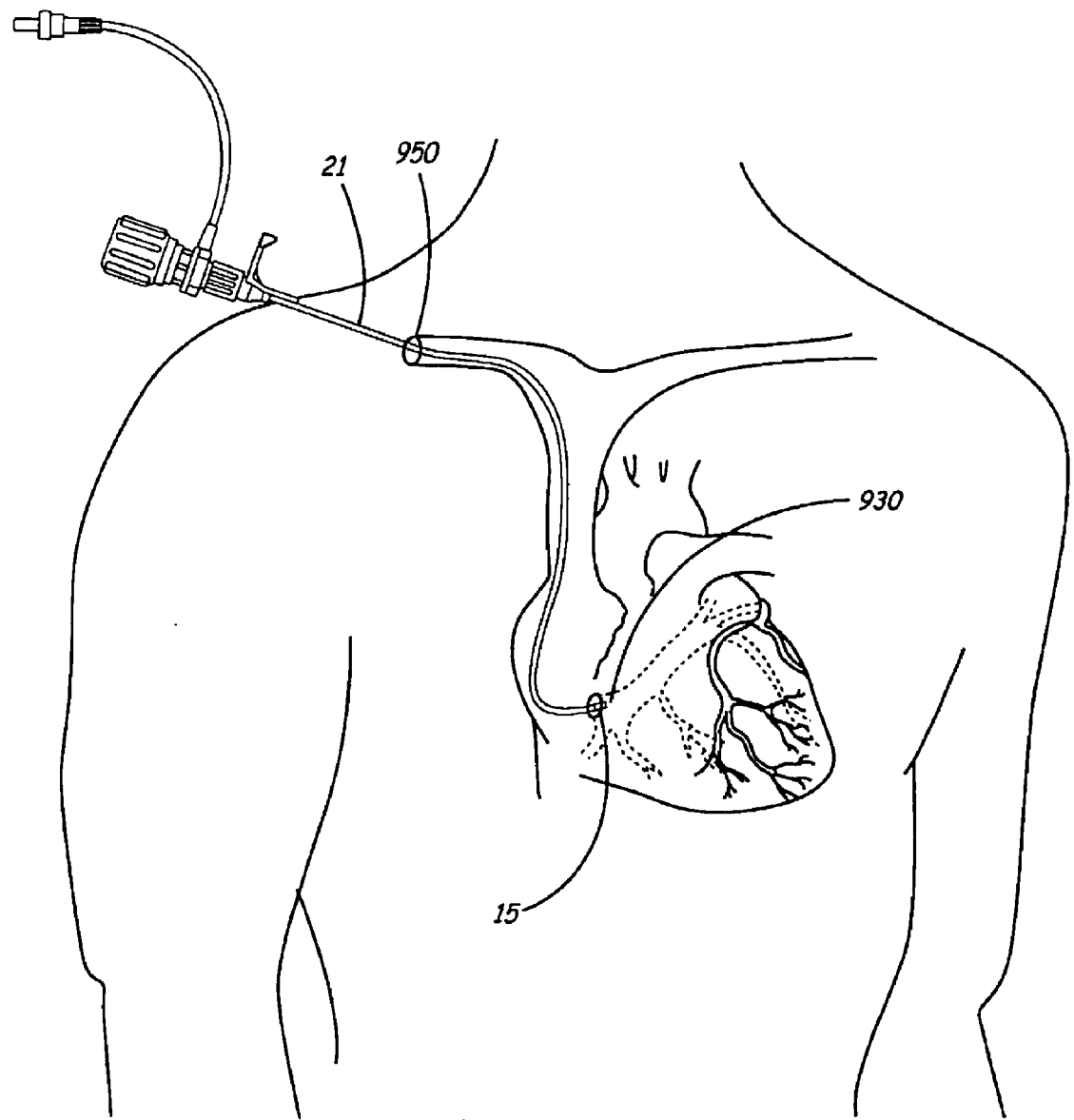
FIG. 17 is a schematic diagram of a delivery sheath for delivering a medical electrical device within a coronary venous system, according to the present invention, from a right-sided venous access point to a coronary sinus.
Figure 18:
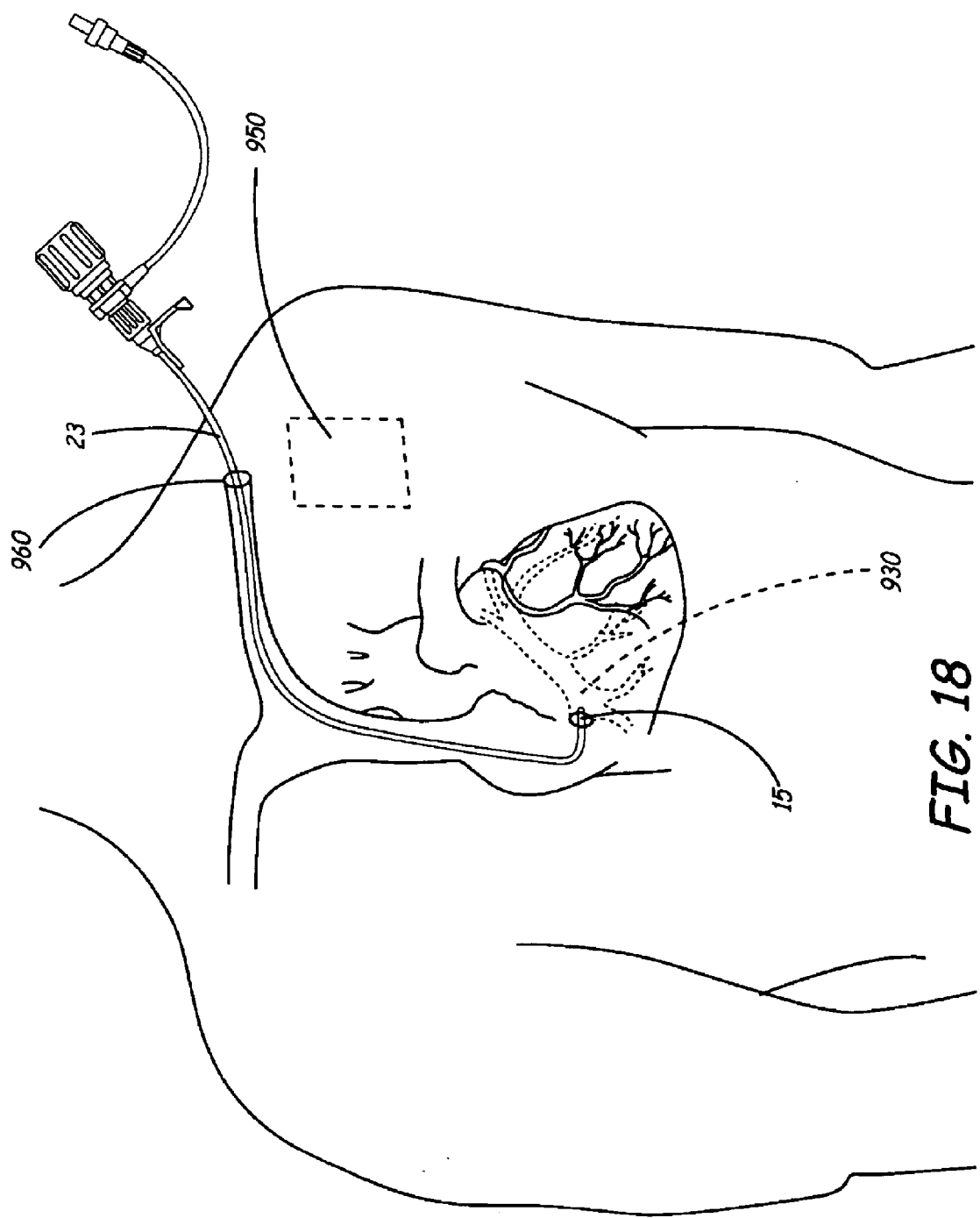
FIG. 18 is a schematic diagram of a delivery sheath for delivering medical devices within a coronary venous system, according to the present invention, from a left-sided venous access point to a coronary sinus.

FIG. 17 is a schematic diagram of a delivery sheath for delivering a medical electrical device within a coronary venous system, according to the present invention, from a right-sided venous access point to a coronary sinus. FIG. 18 is a schematic diagram of a delivery sheath for delivering medical devices within a coronary venous system, according to the present invention, from a left-sided venous access point to a coronary sinus. FIGS. 17 and 18 illustrate the right and left sided approaches, after distal tip 15 of delivery sheath 21, 23 has been seated in the coronary sinus 930. Introducer guide wire 4 or steerable catheter 1002 has been removed from lumen of delivery sheath 21, 23. As illustrated in FIGS. 17 and 18, left-sided venous access point 960 is a greater distance from the ostium of coronary sinus 930 than right-sided venous access point 950, and the approach to the coronary sinus 930, from left-sided venous access point, is not as direct. Left-sided venous access point 960 may be selected because venous anatomy communicating from right-sided access point 950 may be blocked or because a preferred implant site 970 for a medical device that is to be connected with a medical electrical lead is on a left side.

Once a passageway formed by lumen of delivery sheath 21, 23 has been established, as illustrated in FIG. 17 or 18, balloon catheter 20 may be advanced down lumen of delivery sheath 21, 23 and into coronary sinus 930 to obtain a venogram. A smaller guide wire or a smaller steerable catheter or deflection mechanism may be used, within a lumen of balloon catheter 20 in order to guide balloon catheter 20 distally into coronary sinus 930 from distal tip 15 of delivery sheath 21, 23. After obtaining venogram, balloon catheter 20 is removed from delivery sheath 21, 23. A navigation pathway established for delivery of a medical electrical lead is a combination of passageway through delivery sheath 21, 23, into coronary sinus 930, and venogram obtained using balloon catheter 20.

Medical Electrical Leads and Accessory Tools

Figure 19:
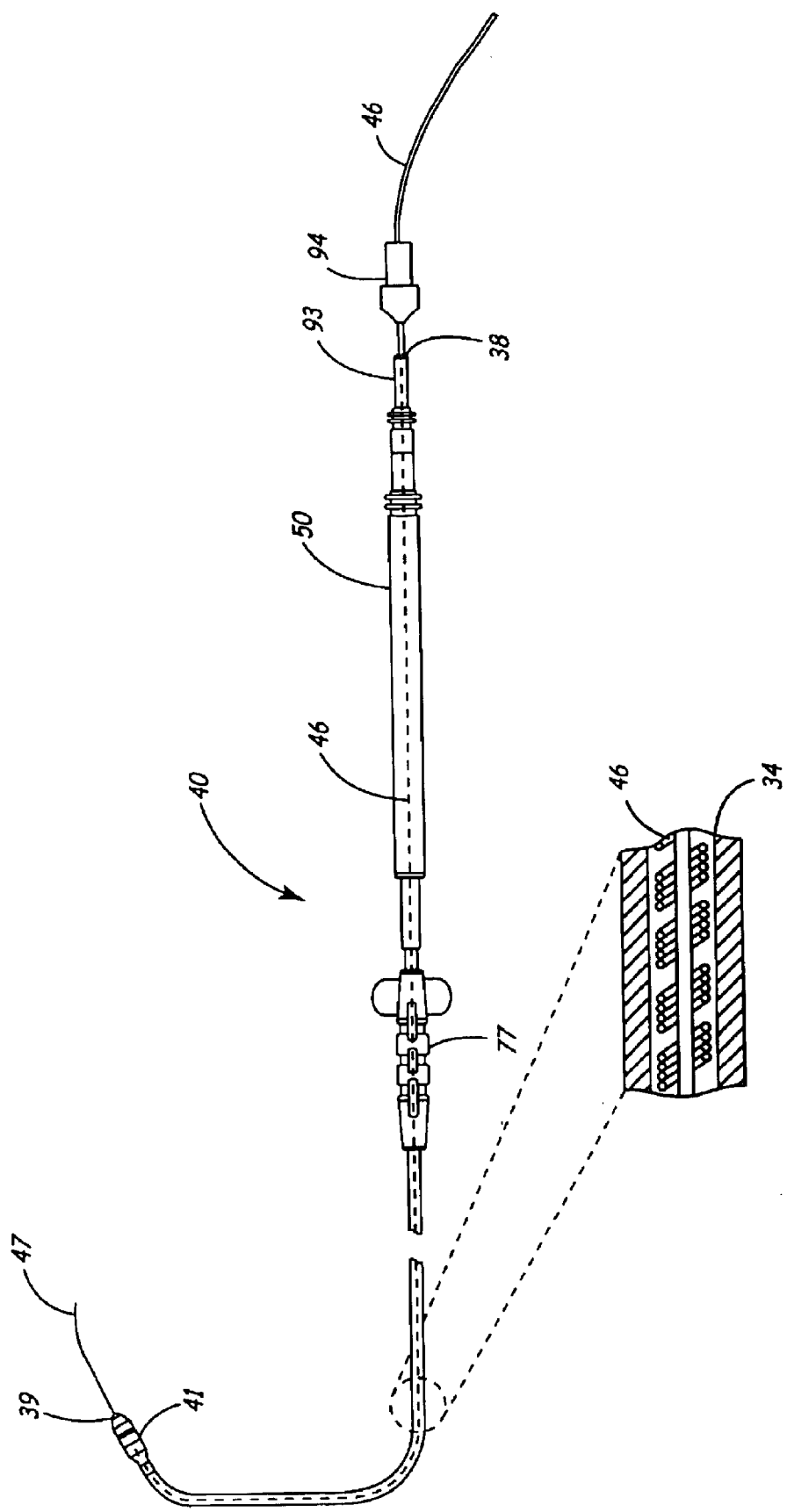
FIG. 19 is a plan view of a medical electrical lead having a lumen for receiving a stylet or a guide wire for delivering a medical electrical device within a coronary venous system according to the present invention.

FIG. 19 is a plan view of a medical electrical lead having a lumen for receiving a stylet or a guide wire for delivering a medical electrical device within a coronary venous system according to the present invention. As illustrated in FIG. 19, a guide wire 46 for introducing a medical electrical lead 40 within the venous system, which is significantly smaller and of a different construction than introducer guide wire 4, is used with delivery sheath 21 or 23. Guide wire 46, which includes an atraumatic formable tip 47, is the same type used with either occlusion balloon catheter 20 or an angioplasty balloon catheter having a construction well known in the art.

FIG. 19 illustrates guide wire 46 inserted into a lumen 34 of lead 40 with formable atraumatic tip 47 protruding from a distal tip 41 of lead 40. Lumen 34 of lead 40 has a diameter between approximately 0.014 inches and 0.022 inches and extends from a proximal opening 38 at a connector pin 93 of a connector 50 of lead 40 to a distal opening 39 in distal tip 41 of lead 40. An anchoring sleeve 77 can also be used to reduce corruption of the lead body caused by suturing once lead 40 has been properly positioned within the venous system. Guide wire 46 is used to steer and guide lead distal tip 41 to a target site in coronary veins by advancing lead 40 over guide wire 46. Such an embodiment of lead 40, called an "over-the-wire lead", is disclosed in commonly assigned U.S. Pat. No. 6,192,280 B1, which is incorporated by reference herein its entirety. A length of guide wire 46 to be used with lead 40 exceeds a length of lead 40, so that tip 47 of guide wire 46 protrudes from distal tip 41 of lead 40, while a proximal portion of guide wire 46 extends proximally from connector pin 93 A guide wire steering tool 94 may be attached to a proximal portion of guide wire 46 to facilitate steering of guide wire 46. According to a preferred embodiment of the present invention, the maximum diameter of guide wire 46 is between approximately 0.012 inches and 0.020 inches.

Figure 20:
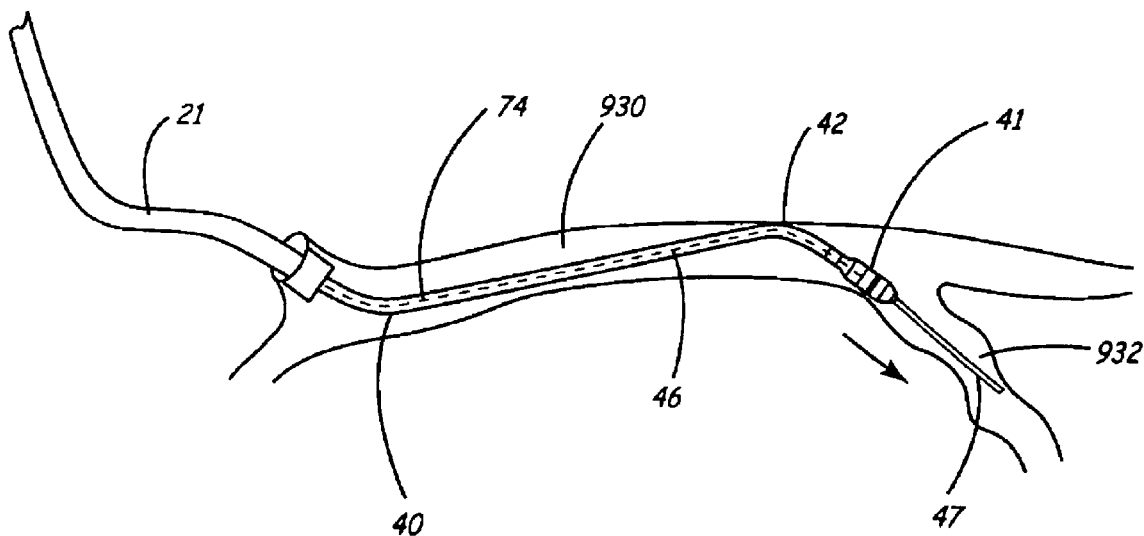
FIG. 20 is a schematic of a guide wire atraumatic formable tip protruding from a lead distal tip of a medical electrical lead and navigating from the coronary sinus into a branch vein.

FIG. 20 is a schematic of a guide wire atraumatic formable tip protruding from a lead distal tip of a medical electrical lead and navigating from the coronary sinus into a branch vein. As illustrated in FIG. 20, guide wire 46, shown by a dashed line, may have been loaded into lumen of lead 40, illustrated in FIG. 19, with loading device 51, illustrated in FIGS. 24–26, then lead 40 and guide wire 46, together, were advanced through delivery sheath 21 to coronary sinus 930. On the other hand, lead 40 could initially be positioned using a stylet wire (FIG. 21), which is then replaced by guide wire 46, or lead 40 could initially be advanced through delivery sheath 21 or 23 and guide wire inserted later. It is therefore understood that many possible ordering of the steps could be used to delivery a medical electrical lead, all of which are merely a matter of operator preference, and therefore the present invention is not intended to be limited to preferred ordering of the steps utilizing the aspects of the present invention, by rather is intended to include the steps performed in any order that is merely a matter of user preference.

A contrast agent could have been injected down lumen of lead 40 to provide real-time fluoroscopic guidance as guide wire tip 47 is manipulated to sub-select branch vein 932. According to the present invention, FIG. 20 illustrates a means for navigating lead tip 41 into branch vein 932. A distal bend 42 of lead 40 provides both guidance and back-up support for guide wire atraumatic formable tip 47 to advance into branch vein 932. Once guide wire tip 47 has cannulated branch vein 932 and is seated deep enough, lead tip 41 can be pushed forward over guide wire 46 to target site in branch vein 932. Guide wire clip 6, illustrated in FIG. 13, may also be used to manage excess length of guide wire 46 in a similar manner to that previously described for introducer guide wire 4 of FIG. 13.

Figure 21:
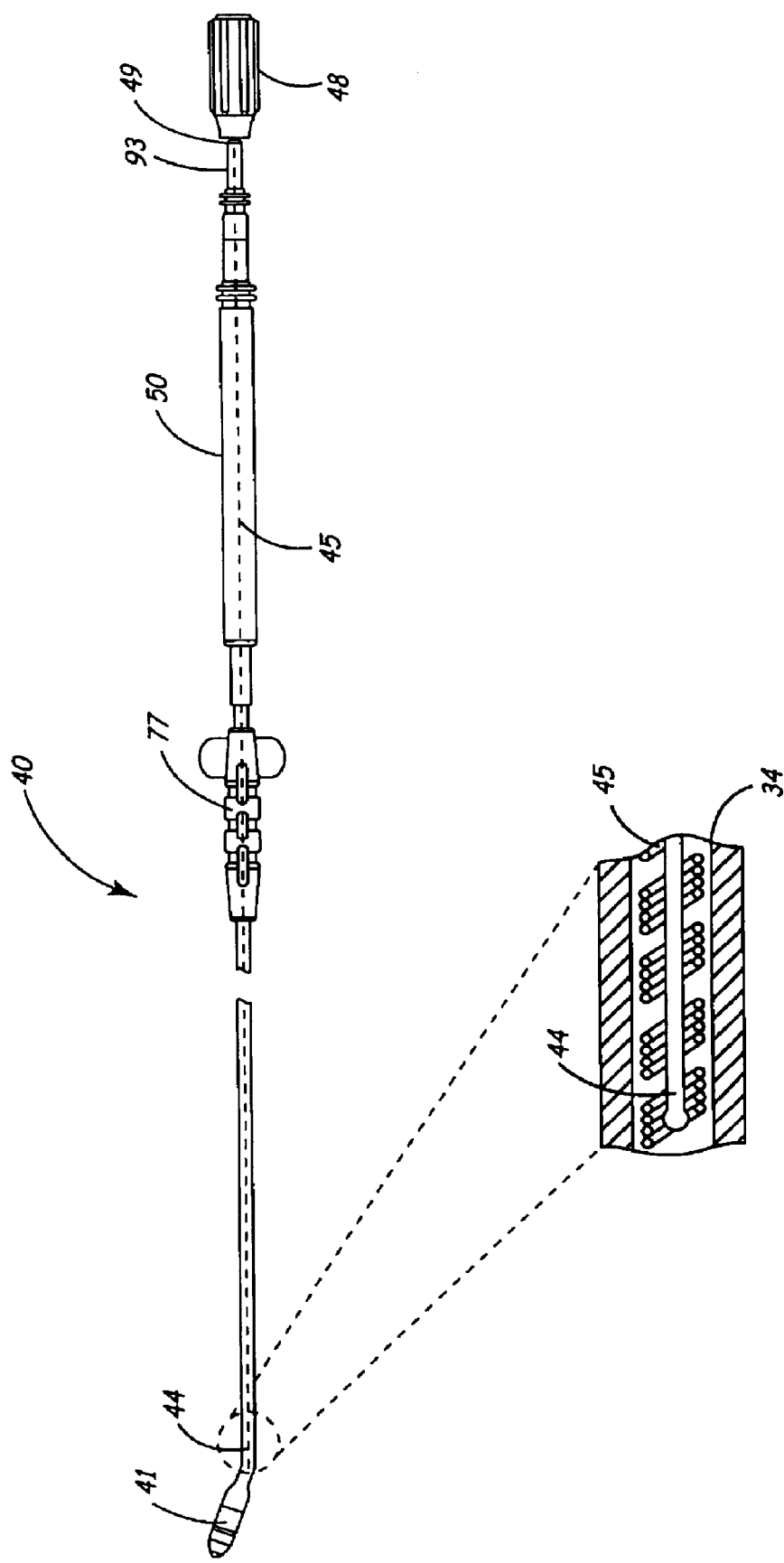
FIG. 21 is a planar view of a stylet inserted within an over-the-wire medical electrical lead in a system for delivering medical devices within a venous system according to the present invention.

FIG. 21 is a planar view of a stylet wire inserted within a medical electrical lead in a system for delivering medical devices within a venous system according to the present invention. As illustrated in FIG. 21, a stylet wire 45, which typically has a greater stiffness than guide wire 46, is insertable within central lumen 34 of medical electrical lead 40 in place of guide wire 46 to assist in the insertion of lead 40 within venous system. Stylet wire 45 includes a distal portion 44, along with a stylet knob 48 attached to a proximal end of stylet wire 45. Stylet wire 45 has a length relative to lead 40 such that once stylet wire 45 is fully inserted within lumen 34, knob 48 of stylet wire 45 engages against connector pin 93 at the proximal end of connector pin 50. As a result, knob 48 of stylet wire 46 prevents further insertion of stylet wire 45 within lumen 34 so that distal portion 44 of stylet wire 45 does not extend outward from distal tip 41 of lead 40. Once fully inserted within lumen 34, stylet wire 45 is subsequently utilized to assist in directing insertion of lead 40 within the venous system.

Figure 22:
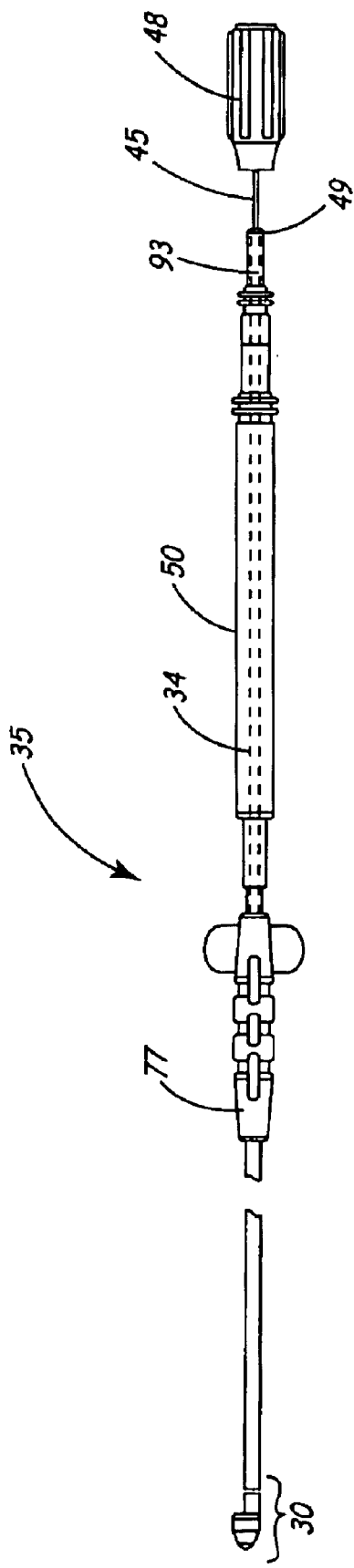
FIG. 22 is planar side view of a medical electrical lead having a lumen for receiving a stylet wire and a guide wire in a system for delivering medical devices within a venous system according to the present invention.
Figure 23:
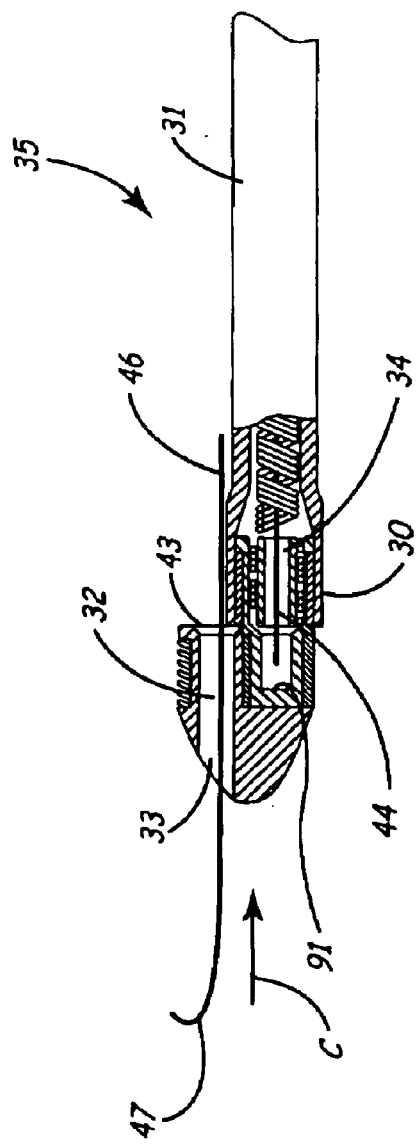
FIG. 23 is a cross-sectional side view of a lead distal tip of the medical electrical lead of FIG. 22.

FIG. 22 is planar side view of a medical electrical lead having a lumen for receiving a stylet wire and a guide wire in a system for delivering medical devices within a venous system according to the present invention. FIG. 23 is a cross-sectional side view of a lead distal tip of the medical electrical lead of FIG. 22. As illustrated in FIGS. 22 and 23, guide wire 46 and stylet wire 45 of tool kit 10 are also insertable within distal tip 30 of a side-lumen lead 35. Similar to over-the-wire lead 40, side-lumen lead 35 includes connector pin 50 and central lumen 34. However, distal tip 30 of lead 35 differs from distal tip 41 of lead 40 since distal tip 30 includes a side lumen 32 that extends from a side lumen distal end 33 to a side lumen proximal end 43. As illustrated in FIG. 23, guide wire 46 is insertable within side lumen 32 by first being inserted at lumen distal end 33 of side lumen 32 in a direction indicated by arrow C, and exiting side lumen 32 at lumen proximal end 43. Once inserted within lumen 32 of lead 35, tip 47 of guide wire 46 is advanced within venous system, so that once tip 47 is positioned at a desired location within the coronary sinus, lead 35 is advanced over guide wire 46 to subsequently position lead distal tip 30 at the desired location, as described below.

In addition, as illustrated in FIGS. 22 and 23, stylet wire 45 may also be inserted within central lumen 34 of lead 35 at opening 49 of connector pin 93 and advanced through lumen 34 to provide additional stiffness for advancing lead 35 within the venous system. As illustrated in FIGS. 22 and 23, lumen 34 of lead 35 extends from opening 49 at connector pin 93 at the proximal end of connector 50 to a lumen end wall 91 located inside distal tip 30 of lead 35. As a result, once stylet wire 45 is fully inserted within lumen 34, distal portion 44 of stylet wire 45 engages against end wall 91, preventing stylet wire 45 from being advanced outward from distal portion 30 of lead 35. Once inserted within lumen 34, stylet wire 45 provides further assistance in directing insertion of lead 35 within the venous system by providing the additional stiffness to lead 35 when advancing distal tip 30 along guide wire 46.

FIG. 24 is a schematic diagram of a loading device in a system for delivering medical devices within a venous system according to the present invention. FIG. 25 is a cross-sectional view of the loading device of FIG. 24. As illustrated in FIGS. 24 and 25, a loading device 51 in a system for delivering medical devices within a venous system according to the present invention includes a navigation portion 54 having an opening 59 formed at a proximal end of loading device 51, an alignment lumen 55 positioned within an alignment shaft 52, and an engagement cavity 58 positioned at a distal end of loading device 51. Opening 59 of navigation portion 54 directs a formable atraumatic tip 47 of guide wire 46 or distal portion 44 of stylet wire 45 within navigation portion 54, which then directs tip 47 or distal portion, respectively, into alignment lumen 55 through a proximal lumen opening 53 of alignment lumen 55.

An inner diameter of engagement cavity 58 is sized to snap-fit connector pin 93 so that a distal lumen opening 56 of loading device 51 is aligned with an opening 49 of lumen 34 of lead 35, 40 at connector pin 93 for continuity between alignment lumen 55 of loading device 51 and lead lumen 34 of lead 35, 40. According to a preferred embodiment of the present invention, engagement cavity 58 includes an inner diameter between approximately 0.059 inches and 0.061 inches and a length between approximately 0.1 inches and 0.2 inches. An engagement cavity wall 59 of engagement cavity 58 forms an opening 74 so that engagement cavity wall 59 does not completely enclose connector pin 93 when connector pin 93 is inserted within engagement cavity 58. As a result, electrical contact can be made with connector pin 93 when loading device 51 and connector pin 93 are fixedly engaged.

Figure 26:
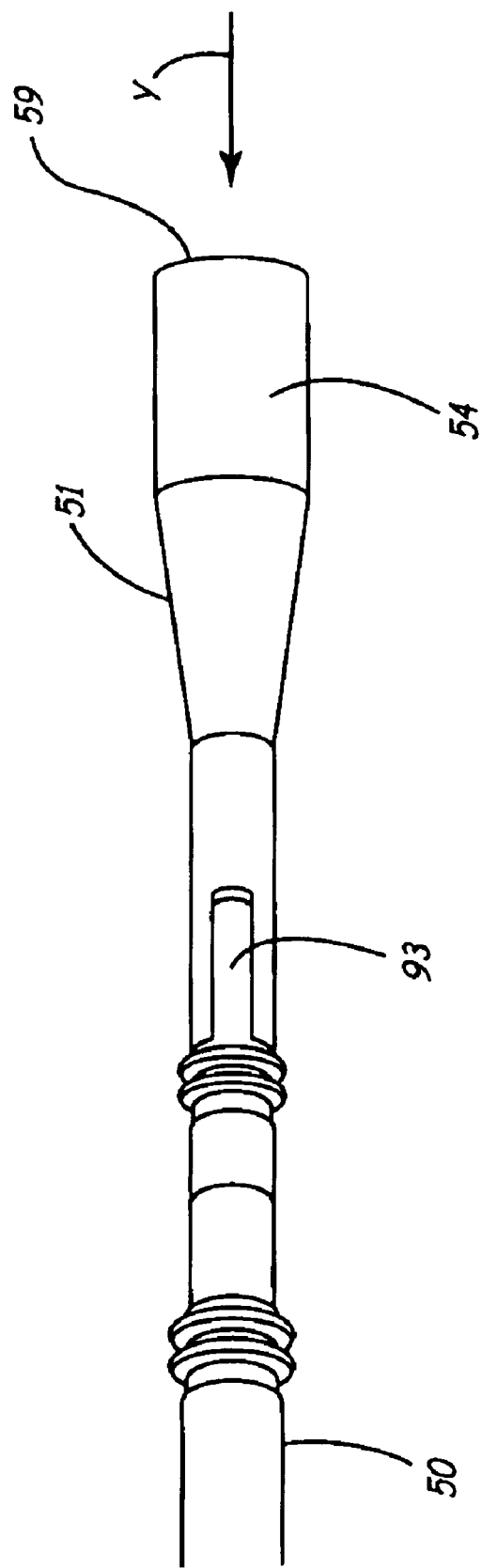
FIG. 26 is a schematic diagram of a lead connector fixedly inserted within the loading tool of FIG. 24.

FIG. 26 is a schematic diagram of a lead connector fixedly inserted within the loading device of FIG. 24. In particular, as illustrated in FIG. 26, once connector pin 93 of connector 50 is fixedly inserted within cavity 58 of loading device 51, tip 47 of guide wire 46 or distal portion 44 of stylet wire 45 is inserted at opening 59 of navigation portion 54 in a direction shown by arrow Y, and is directed within lumen opening 53 of alignment lumen 55 by navigation portion 54. Tip 47 or distal portion 44 is then directed through alignment lumen 55 towards distal lumen opening 56. Since opening 56 is aligned with opening 49 of lumen 34 of connector 50 at connector pin 93, tip 47 or distal portion 44 passes through openings 56 and 49 and into lumen 34 of connector 50.

According to the present invention, if loading tool 51 is utilized to load stylet wire 45, loading tool 51 and hemostasis valve 27 are sized so that hemostasis valve 27 can be advanced over loading tool 51 and stylet knob 48 to remove hemostasis valve 27 from lead 35, 40 once lead 35, 40 is advanced within the coronary venous system to a target site, as described below.

Figure 27:
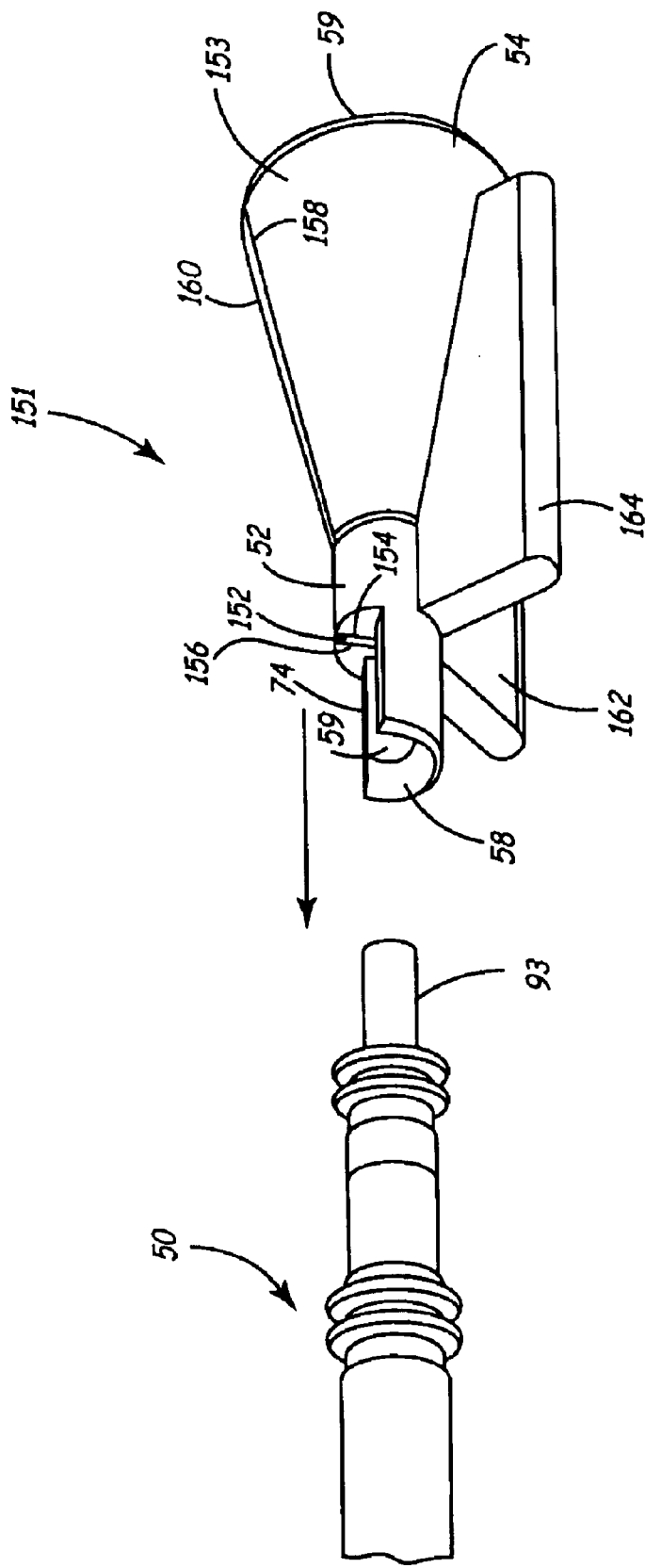
FIG. 27 is an isometric diagram of an alternate embodiment of a loading tool in a system for delivering medical devices within a venous system according to the present invention.

FIG. 27 is an isometric diagram of an alternate embodiment of a loading device in a system for delivering medical devices within a venous system according to the present invention. As illustrated in FIG. 27, a loading device 151, according to an alternate preferred embodiment of the present invention is similar to loading device 51 described above in reference to FIGS. 24 and 25 above. Accordingly, loading device 151 fixedly engages with connector pin 93 in a manner as described above in reference to FIGS. 24 and 25, and therefore a description of the similar features, indicated by like reference numerals, is omitted merely for brevity.

Figures 28, 30:
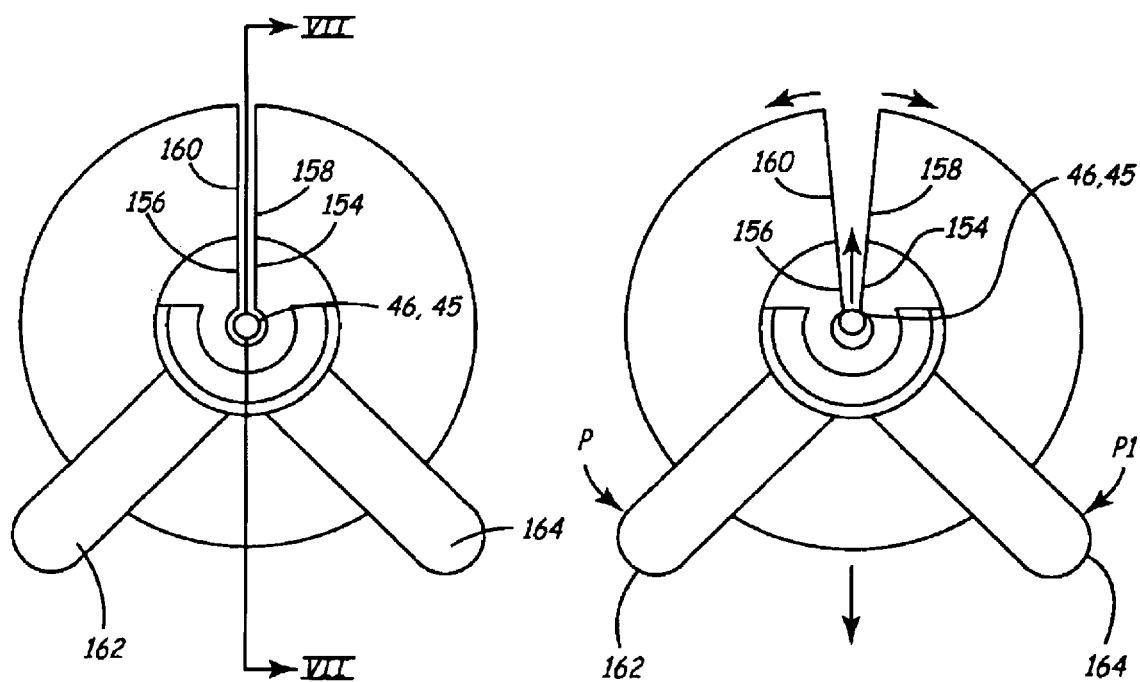
FIG. 28 is a front planar view of the loading tool of FIG. 27 in a closed position.
FIG. 30 is a front planar view of the loading tool of FIG. 27 in an open position.
Figure 29:
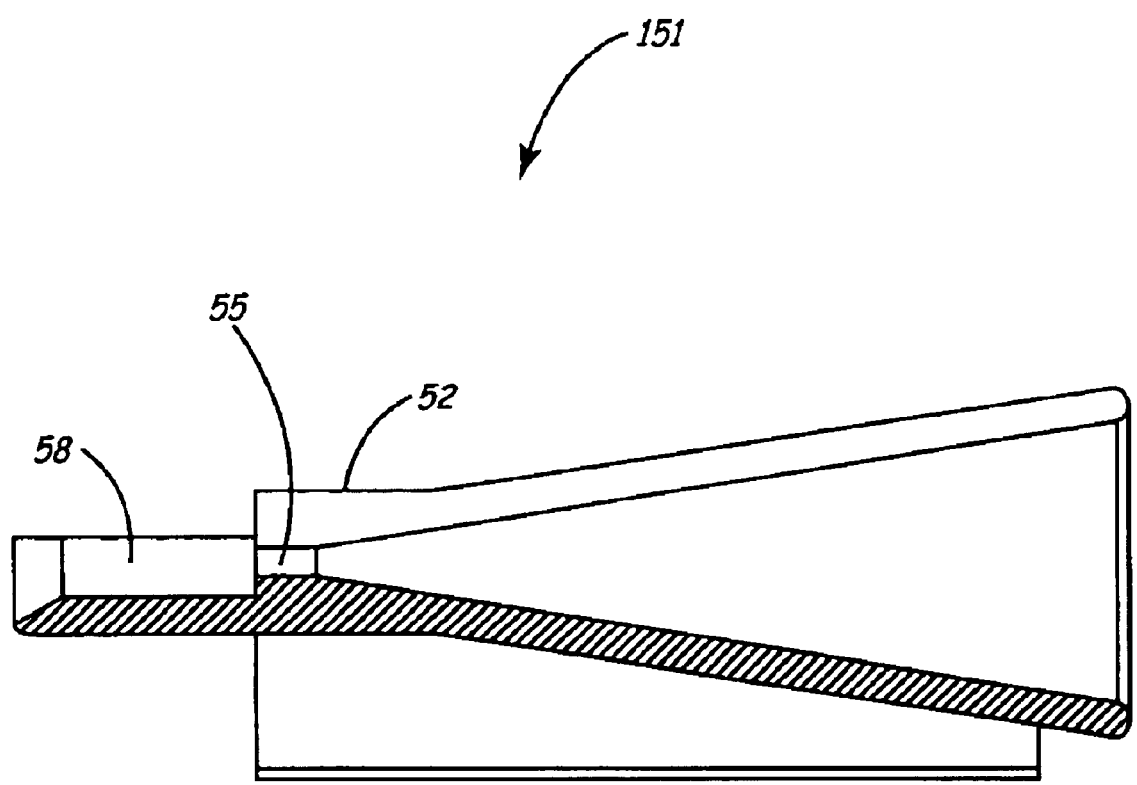
FIG. 29 is a cross-sectional side view of a loading tool according to the present invention, taken along cross-sectional lines VII—VII of FIG. 28.

FIG. 28 is a front planar view of the loading device of FIG. 27 in a closed position. FIG. 29 is a cross-sectional side view of a loading device according to the present invention, taken along cross-sectional lines VII—VII of FIG. 28. As illustrated in FIGS. 27–29, similar to loading device 51, loading device 151 includes engagement cavity 58, alignment shaft 52, and navigation portion 54 forming opening 59. However, according to an alternate embodiment of the present invention, loading device 151 includes a slot 152 extending from the distal end of alignment shaft 52 to the proximal end of navigation portion 54 at opening 59. As illustrated in FIGS. 27 and 28, slot 152 extends through an outer wall 153 of navigation portion 54 and through alignment shaft 52 to alignment lumen 55 (FIG. 29) and is defined by a first side wall 154 of alignment shaft 52 adjacent a second side wall 156 of alignment shaft 52, and a first side wall 158 of outer wall 153 of navigation portion 54 adjacent a second side wall 160 of outer wall 153 of navigation portion 54. Loading device 151 also includes spaced flange portions 162 and 164 extending from the distal end of alignment shaft 52 and terminating along outer wall 153 of navigation portion 54. A distance between side walls 154–160 of slot 152 is less than the diameter of guide wire 46 or stylet wire 45 when slot 152 of loading device 151 is in a closed position, illustrated in FIG. 28. As a result, loading device 151 cannot be removed directly from guide wire 46 or stylet wire 45 when slot 152 of loading device 151 is in the closed position.

FIG. 30 is a front planar view of the loading device of FIG. 27 in an open position. As illustrated in FIG. 30, once pressure is applied at flange portions 162 and 164 in a direction shown by arrows P and P', respectively, the applied pressure causes flange portions 162 and 164 to be displaced relative to each other so that a distance between flange portions 162 and 164 is reduced, and slot 152 of loading device 151 is moved from the closed position of FIG. 28 to an open position, shown in FIG. 30. The relative displacement of flange portions 162 and 164 causes side walls 154–160 of slot 152 to be displaced so that the distance between side walls 154–160 of slot 152 is greater than the diameter of guide wire 46 or stylet wire 45, so that loading device 151 can be directly removed from guide wire 46 or from stylet wire 45 through slot 152 when slot 152 is in the open position.

Figure 31:
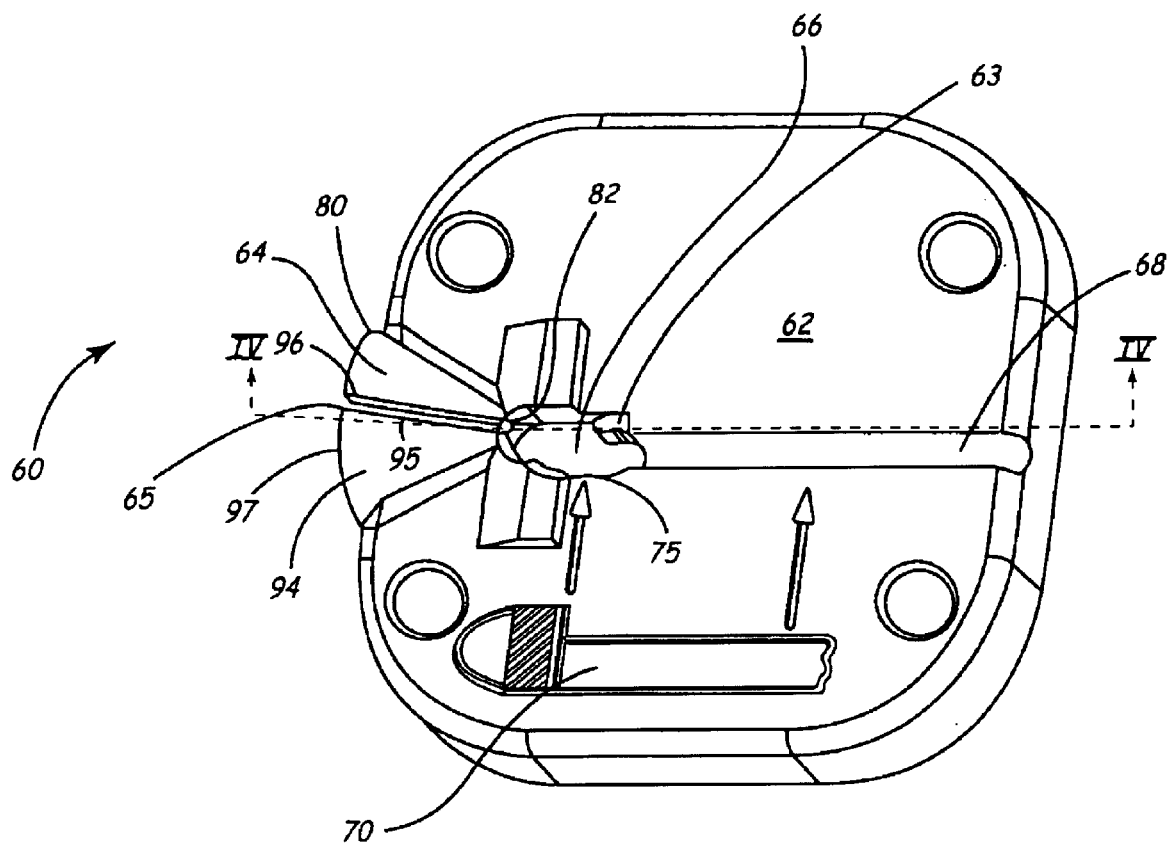
FIG. 31 is a top perspective view of a loading tool for loading a guide wire within a medical electrical lead according to the present invention.

FIG. 31 is a top perspective view of an alternate embodiment of a loading device for loading a guide wire within a medical electrical lead according to the present invention. As illustrated in FIG. 31, a loading device 60 according to an alternate embodiment of the present invention includes a navigating portion 64 extending from a front end 80 to a back end 82. Navigation portion 64 includes an outer portion 94 and a first side wall 95 spaced apart from a second side wall 96 to form a slot 65 that extends from front end 80 to back end 82 of navigation portion 64. An opening 75 is formed at back end 82 of navigation portion 64 and couples navigation portion 64 with an engagement cavity 66. Navigation portion 64 receives guide wire 46 as guide wire 46 is inserted within an opening 97 formed at front end 80 and directs guide wire 46, as guide wire 46 is inserted within navigation portion 64, towards opening 75 at back end 82.

Guide wire 46 is then directed within engagement cavity 66 through opening 75 at back end 82.

Loading device 60 also includes engagement cavity 66 and a lead slot 68 for receiving and positioning lead tip 30 and a lead body distal portion 31, respectively, within loading device 60. An insertion guide 70 is formed on an upper surface 62 of loading device 60 to assist the user in properly positioning lead 35 for insertion within engagement cavity 66 and lead slot 68. Engagement cavity 66 is shaped to form a line-to-line or minimum clearance fit around lead distal tip 30 to orientate lead distal tip 30 to be in a position corresponding to the orientation indicated by insertion guide 70 in order to prevent lead distal tip 30 from being corrupted when lead distal tip 30 is inserted within engagement cavity 66. For example, according to a preferred embodiment of the present invention, engagement cavity 66 is sized to extend approximately 0.002 inches from lead distal tip 30 when lead distal tip 30 is positioned within engagement cavity. On the other hand, lead slot 68 is shaped to engage lead body distal portion 31 to snap-fit lead body distal portion 31 within lead slot 68.

Back end 82 of navigation portion 64 is located along engagement cavity 66 so that back end 82 is aligned with side lumen 32 of lead tip 30 at lumen distal end 33 when lead tip 30 is inserted within engagement cavity 66 in a position corresponding to the orientation indicated by insertion guide 70 and lead body distal portion 31 is snap-fit to be fixedly engaged within lead slot 68. As a result, loading device 60 of the present invention enables guide wire 46 to be more easily inserted within side lumen 32 of lead tip 30, as will be described below.

Figure 32:
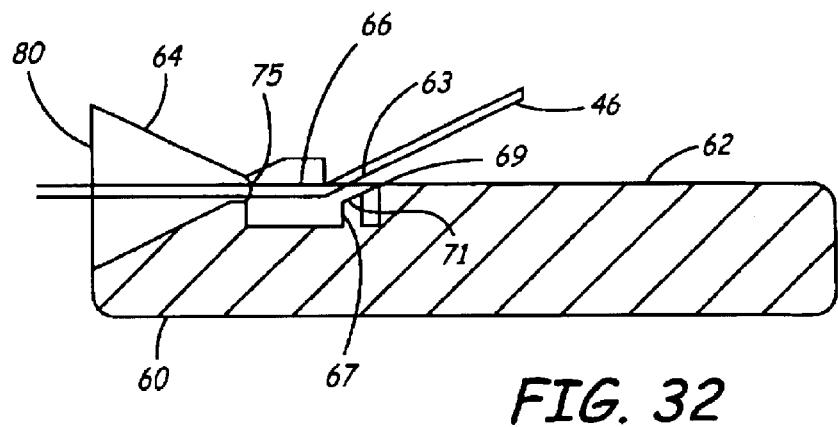
FIG. 32 is a cross-sectional side view of a loading tool according to the present invention, taken along cross-sectional line IV—IV of FIG. 31.

FIG. 32 is a cross-sectional side view of a loading device according to the present invention, taken along cross-sectional line IV—IV of FIG. 31. As illustrated in FIGS. 31 and 32, a ramp portion 63 is formed in engagement cavity 66 of loading device 60. Ramp portion 63 extends from a lower end 67 to an upper end 69 to form an upward extending surface 71 that directs guide wire 46 out of engagement cavity 66 as guide wire 46 is inserted within navigation portion 64 of loading device 60 and through side lumen 32 of lead 35 once lead 35 is inserted within engagement cavity 66 and lead slot 68 of loading device 60, as described below.

Figure 33:
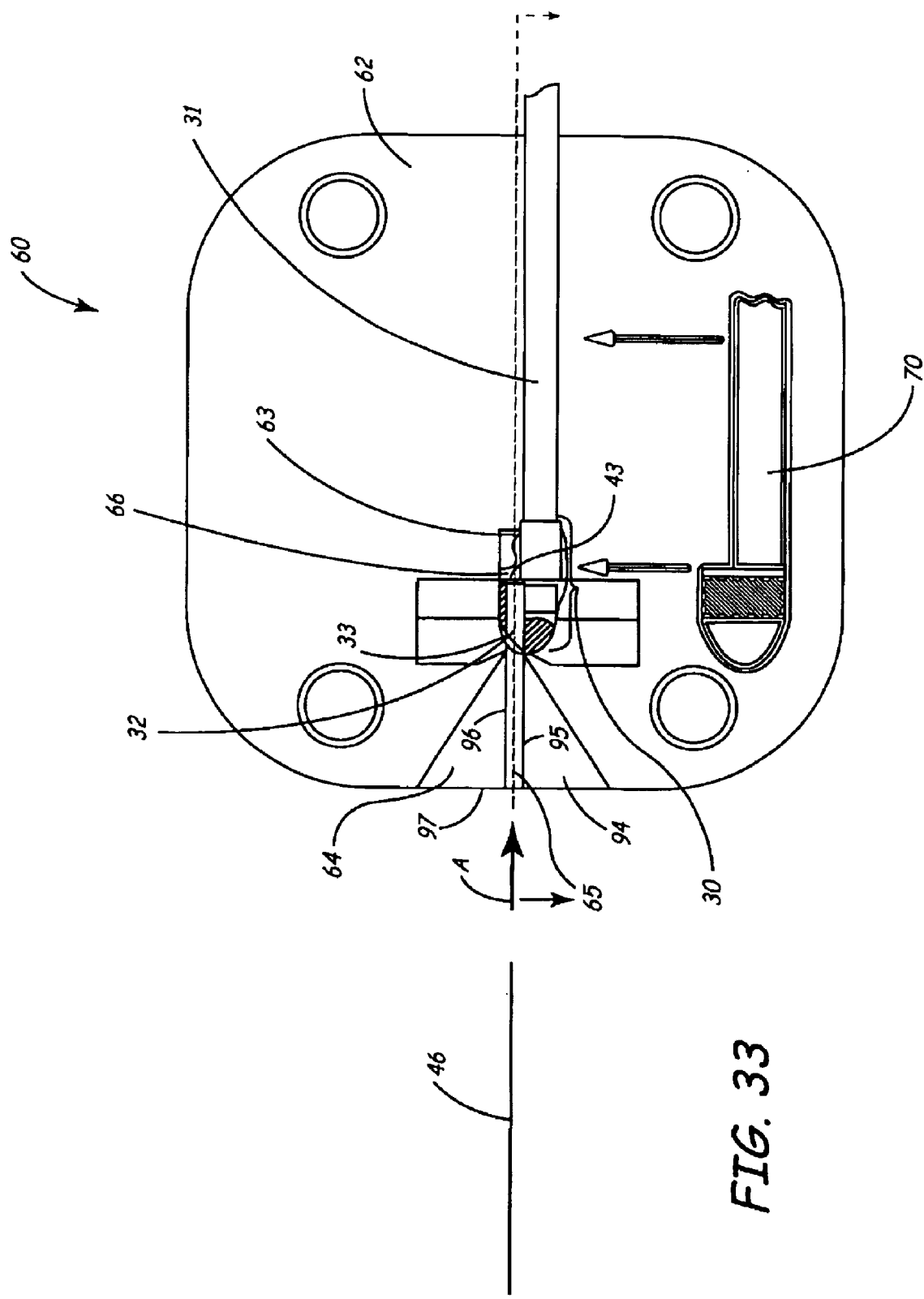
FIG. 33 is a top planar view illustrating insertion of a guide wire within a medical electric lead using a loading tool according to the present invention.
Figure 34:
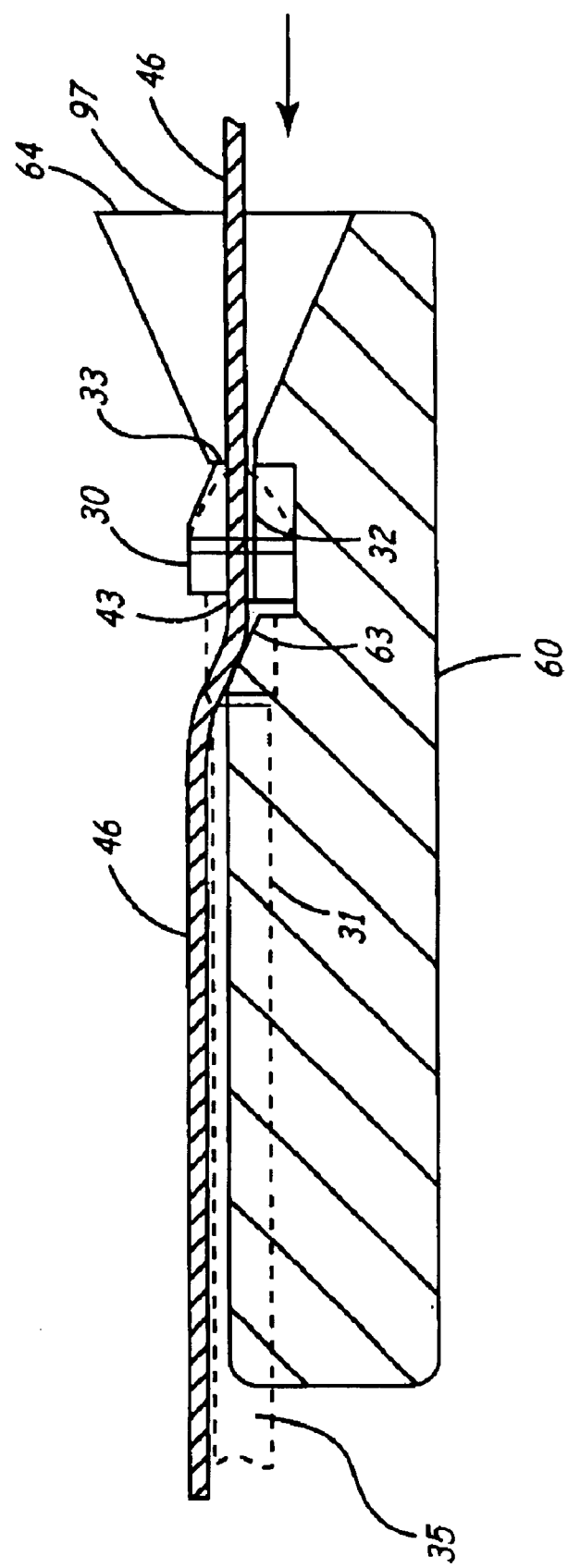
FIG. 34 is a cross-sectional side view of a loading tool according to the present invention, taken along cross-sectional lines V—V of FIG. 33.

FIG. 33 is a top planar view illustrating insertion of a guide wire within a medical electric lead using a loading device according to the present invention. FIG. 34 is a cross-sectional side view of a loading device according to the present invention, taken along cross-sectional lines V—V of FIG. 33. As illustrated in FIGS. 33 and 34, lead 35 is inserted within loading device 60 by positioning lead tip 30 to match an orientation depicted by insertion guide 70, and once lead tip 30 is oriented in the same position as shown by insertion guide 70, lead 35 is positioned within loading device 60 by inserting lead tip 30 within engagement cavity 66 and snap-fitting lead body distal portion 31 within lead slot 68 of loading device 60 to fixedly engage lead body distal portion 31 within loading device 60.

Once positioned within engagement cavity 66, distal end 33 of side lumen 32 of lead 35 is aligned with opening 75 of navigation portion 64. After lead 35 is inserted within loading device 60, guide wire 46 is inserted within navigation portion 64 in a direction A. By aligning opening 75 of navigation portion 64 with distal end 33 of side lumen 32, once navigation portion 64 guides wire 46 to be advanced through opening 75, loading device 60 directs guide wire 46 to be advanced within lumen distal end 33 of side lumen 32 of lead 35. As guide wire 46 is advanced through side lumen 32, and guide wire 46 subsequently exits side lumen 32 at lumen proximal end 43, ramp portion 63 directs guide wire 46 out of engagement cavity 66 as guide wire 46 is extended through side lumen 32 of lead tip 30.

According to a preferred embodiment of the present invention, upper surface 62 of loading device 60 which is approximately one inch square with a thickness between approximately 0.15 inches and 0.25 inches, provides a platform that can easily be held by an operator while engaging lead body distal portion 31 and lead distal tip 30, and directing guide wire 46 into side lumen 32. Surface of handling interface 62 is also large enough to fit etched insertion guide 70 depicting lead body distal portion 31 and distal tip 30 at a 1:1 scale. Insertion guide 70 aids operator in correct placement of lead distal tip 30 into engagement cavity 66.

According to the present invention, first side wall 95 is spaced from second side wall 96 at a distance that enables guide wire 46 to be advanced between first side wall 95 and second side wall 96. As a result, once guide wire 46 is positioned within side lumen 32, lead 35 is removed from loading device 60 with guide wire 46 positioned through side lumen 32 by removing distal portion 31 and lead distal tip 30 of lead 35 from lead slot 68 and engagement cavity 66, respectively, and removing guide wire 46 from within navigation portion 64 by advancing guide wire 46 through slot 65.

Figure 35:
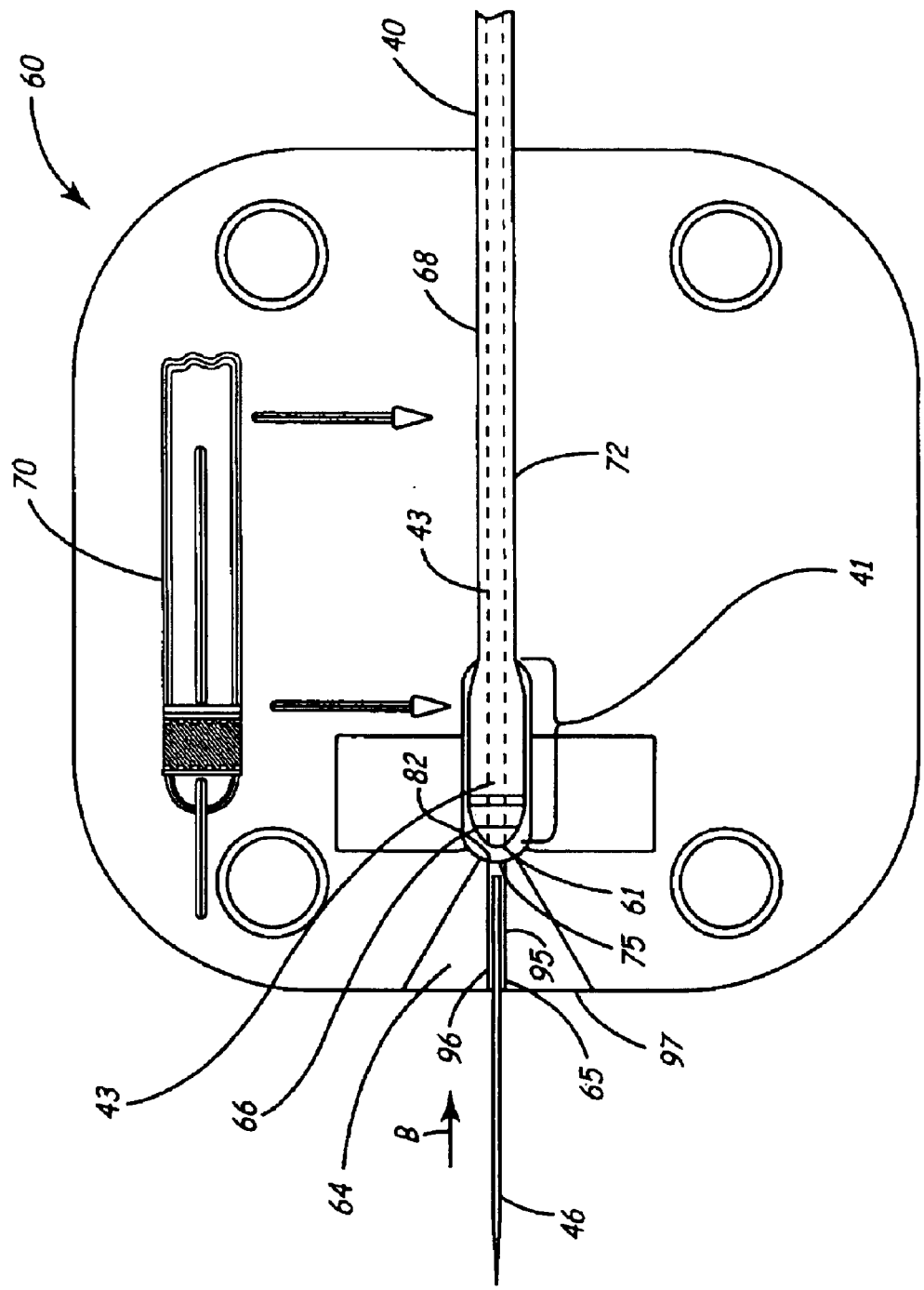
FIG. 35 is a top planar view illustrating insertion of a guide wire within a medical electric lead using an alternate embodiment of a loading tool according to the present invention.

FIG. 35 is a top planar view illustrating insertion of a guide wire within a medical electric lead using an alternate embodiment of a loading device according to the present invention. The alternate embodiment of loading device 60 differs in that loading device 60 is formed to enable loading of guide wire 46 within an over-the-wire lead 40 having a lead distal tip 41 with a lumen 43 centrally located to extend through lead 40 from a distal end 61 of lead distal tip 41. In particular, as illustrated in FIG. 35, according to the alternate embodiment of the present invention, engagement cavity 66 of loading device 60 is formed to receive lead distal tip 41 to assist in the insertion of guide wire 46 within lead 40. Lead 40 is inserted within loading device 60 by positioning lead distal tip 41 to match an orientation depicted by insertion guide 70, and once lead distal tip 41 is oriented in the same position as shown by insertion guide 70, lead 40 is positioned within loading device 60 by inserting lead tip 41 within engagement cavity 66 and a lead body distal portion 72 within lead slot 68 of loading device 60.

Engagement cavity 66 is shaped to form a line-to-line or minimum clearance fit around lead distal tip 41 to orientate lead distal tip 41 to be in a position corresponding to the orientation indicated by insertion guide 70 in order to prevent lead distal tip 41 from being corrupted when inserted within engagement cavity 66. For example, according to a preferred embodiment of the present invention, engagement cavity 66 is sized to extend approximately 0.002 inches from lead distal tip 41 when lead distal tip 41 is positioned within engagement cavity 66. On the other hand, lead slot 68 is shaped to engage lead body distal portion 72 to snap-fit lead body distal portion 72 within lead slot 68. In addition, similar to the preferred embodiment described above in reference to FIGS. 31–34, back end 82 of navigation portion 64 is located along engagement cavity 66 so that back end 82 is aligned with lumen 43 at lumen distal end 61 when lead distal tip 41 is inserted within engagement cavity 66 in a position corresponding to the orientation indicated by insertion guide 70 and lead body distal portion 72 is snap-fit to be fixedly engaged within lead slot 68. As a result, loading device 60 of the present invention enables guide wire 46 to be more easily inserted within lumen 43 of lead distal tip 41.

After lead 40 is inserted within loading device 60, guide wire 46 is inserted within navigation portion 64 at opening 97 in direction B, with navigation portion 64 directing guide wire 46 towards opening 75 so that guide wire 46 is inserted within lead distal tip 41 at lumen distal end 61 of lumen 43. Guide wire 46 is directed into lumen 43 at distal tip 41, passes through lumen 43, and travels out proximal opening in connector pin 50 (FIG. 21). Once guide wire 46 is positioned within lumen 43, lead 40 is removed from loading device 60 with guide wire 46 positioned through lumen 43 by removing lead distal tip 41 and distal portion 72 of lead 40 from engagement cavity 66 and lead slot 68, respectively, and removing guide wire 46 from within navigation portion 64 by advancing guide wire 46 through slot 65.

Figure 36:
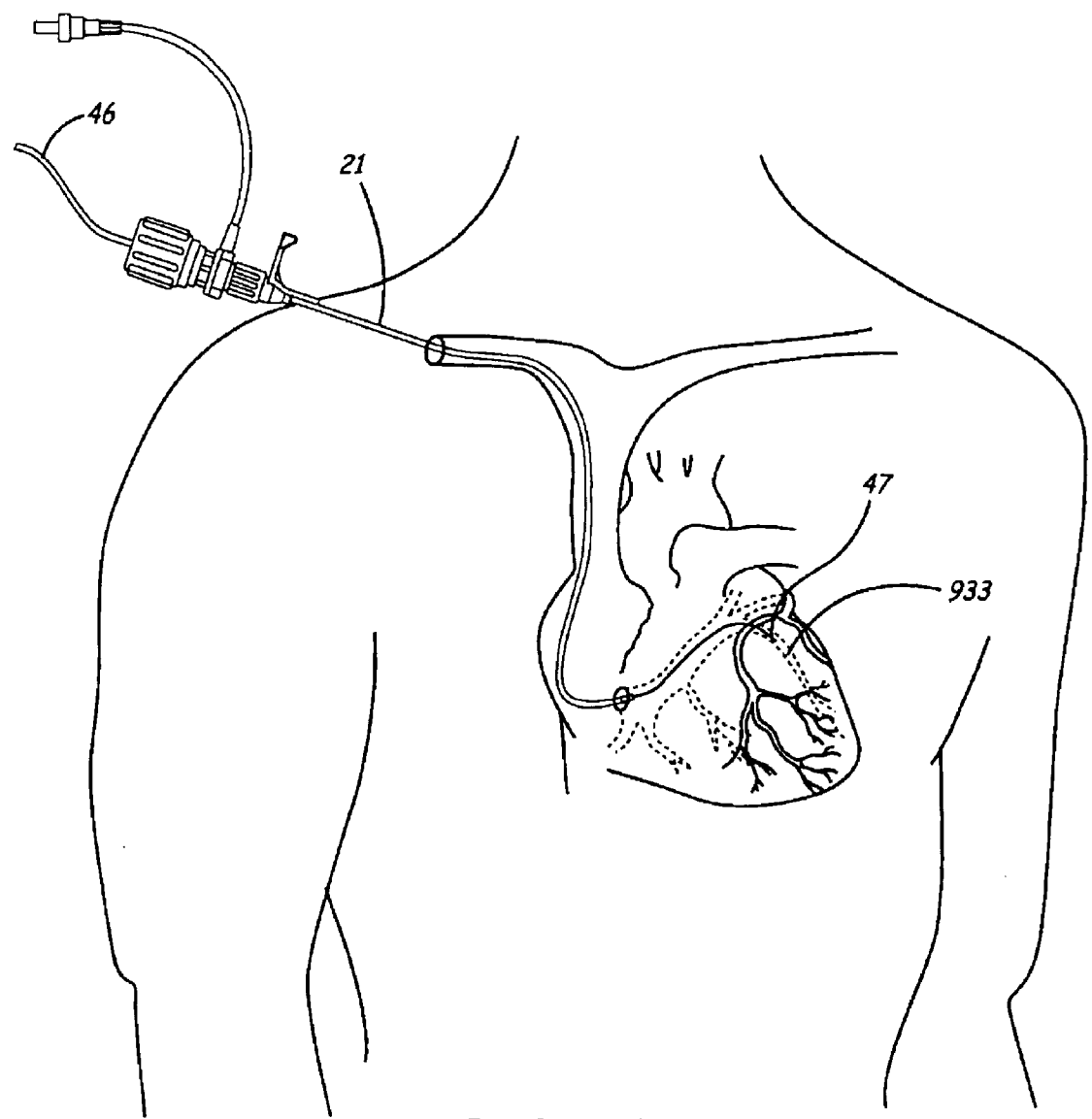
FIG. 36 is a schematic diagram of positioning of a guide wire 46 within a branch vein.

FIG. 36 is a schematic diagram of positioning of a guide wire 46 within a branch vein. According to the present invention, FIG. 36 illustrates a situation in which guide wire 46 was used to deliver venogram balloon catheter 20, illustrated in FIG. 13, through delivery sheath 21. After obtaining venogram with balloon catheter 20, atraumatic formable tip 47 of guide wire 46 is advanced to a target site in branch vein 933; positioning of atraumatic formable tip 47 may have been facilitated by additional injections of a contrast agent down a lumen of balloon catheter 20. Guide wire 46 is left in position when balloon catheter 20 is removed. Proximal end of guide wire 46 may be directed into side lumen 32 of lead tip 30, illustrated in FIGS. 21 and 22 and 32, using loading device 60 as illustrated in FIG. 31. Lead tip 30 is pushed along guide wire 46 until lead tip 30 reaches the target site in branch vein 933. As illustrated in FIGS. 21 and 22, stylet wire 45 may be inserted into central lumen 34 of lead 35 to provide additional stiffness for moving lead distal tip 30 along guide wire 46.

Guide wire 46 and /or stylet wire 45 may be removed before delivery sheath 21 is removed, however a preferred method is to retain guide wire 46 and /or stylet wire 45 until after delivery sheath 21 is removed. A retained stylet wire 45 helps maintain stiffness in lead 35 that can be used to hold lead tip 30 in position while delivery sheath 21 is being removed. If removal of delivery sheath 21 dislodges lead tip 30, a retained guide wire 46 will help to re-position lead tip 30.

Figure 37:
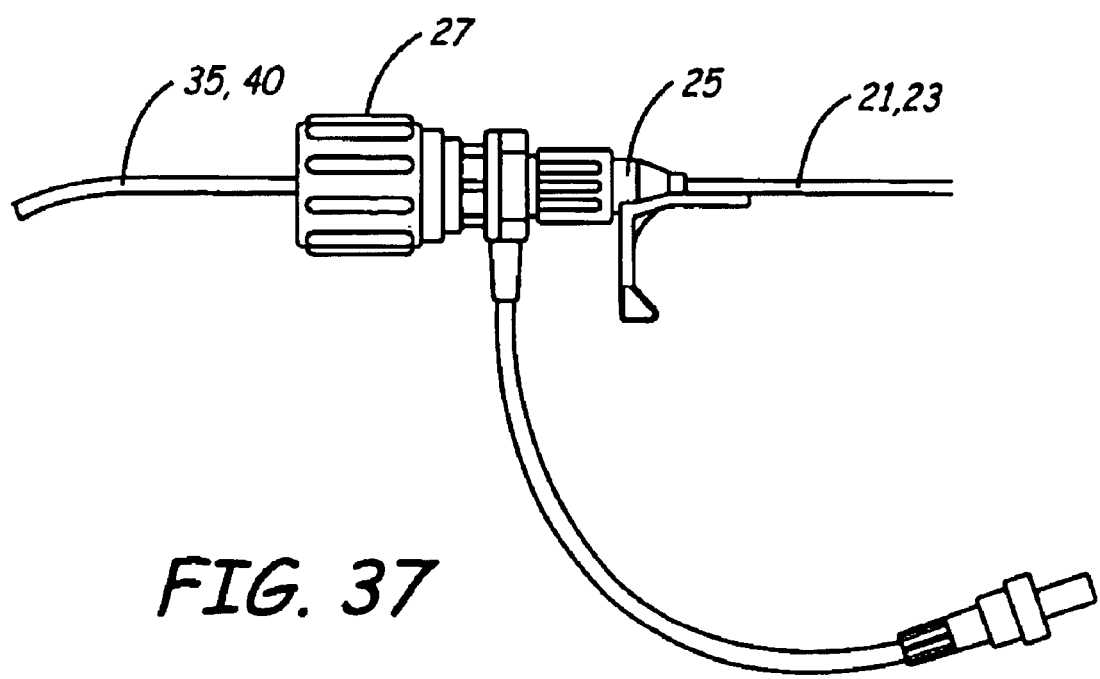
FIG. 37 is a schematic diagram of a hemostasis valve according to the present invention in an attached position.
Figure 38:
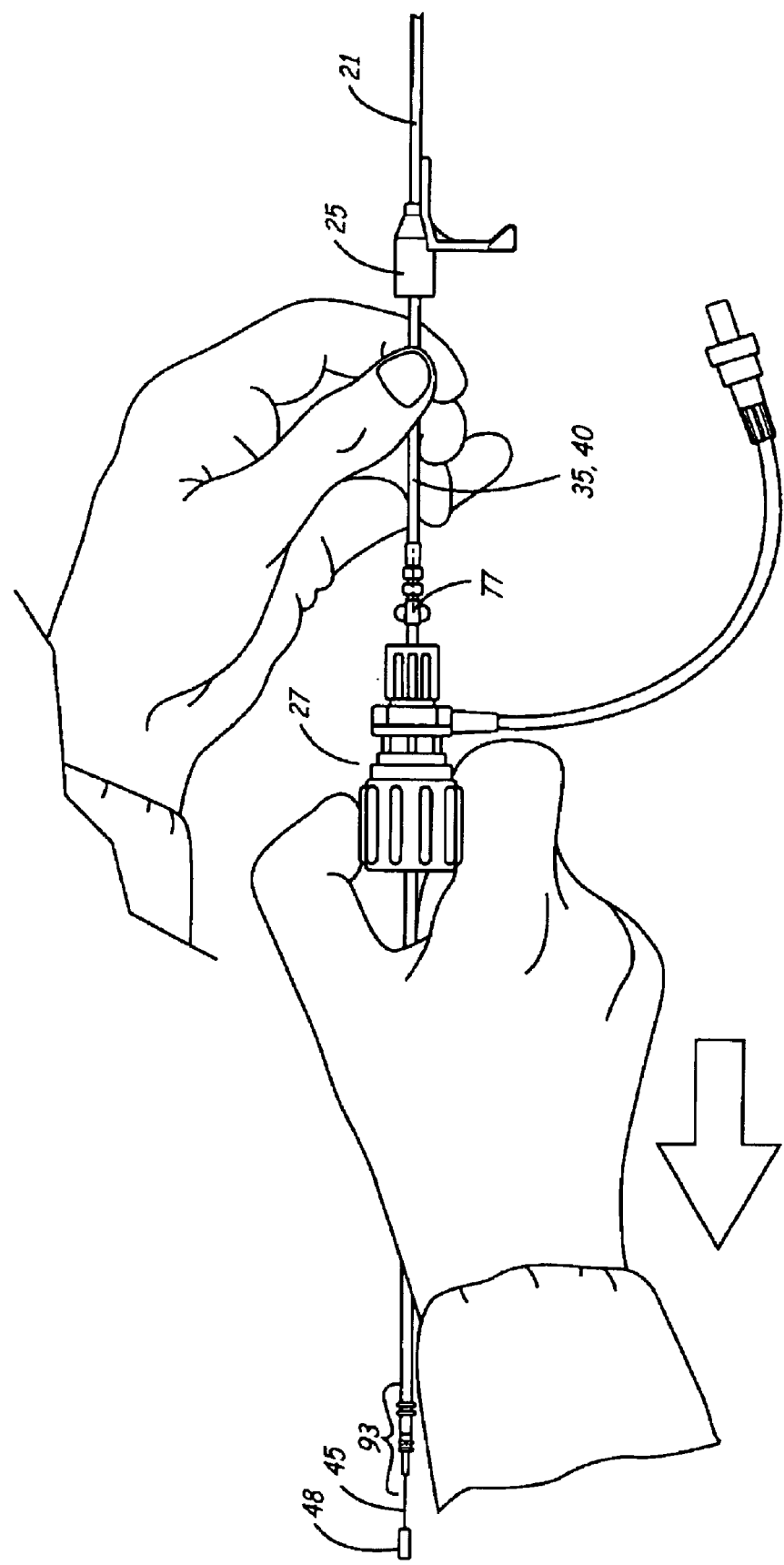
FIG. 38 is a schematic diagram of a hemostasis valve according to the present invention in an unattached position.

FIGS. 37 and 38 are schematic diagrams illustrating removal of a delivery sheath and a rotatable hemostasis valve from an implanted lead body according to the present invention. Once insertion of the lead has been completed, delivery sheath 21, 23 must be slit and peeled off from lead body 35, 40 since outer diameters of an industry standard IS-1 connector 50 and an anchoring sleeve 77, mounted on lead body 73, are significantly larger than a diameter of lead body 35, 40 and will not fit through lumen of delivery sheath 21. In addition, hemostasis valve 27 must also be removed from lead body 35, 40. According to the present invention, hemostasis valve 27 is first removed from hub 25 of sheath 21, 23 by rotating collar 37 to unlock hemostasis valve 27 from hub 25. Once unlocked from hub 25, hemostasis valve 27 is slid over lead 35, 40 to advance hemostasis valve 27 from an attached position, illustrated in FIG. 37, to an unattached position, illustrated in FIG. 38, so that hemostasis valve 27 is slid over anchoring sleeve 77 and connector 50, and over knob 48 of stylet wire 45, if stylet wire 45 is utilized.

Figure 39:
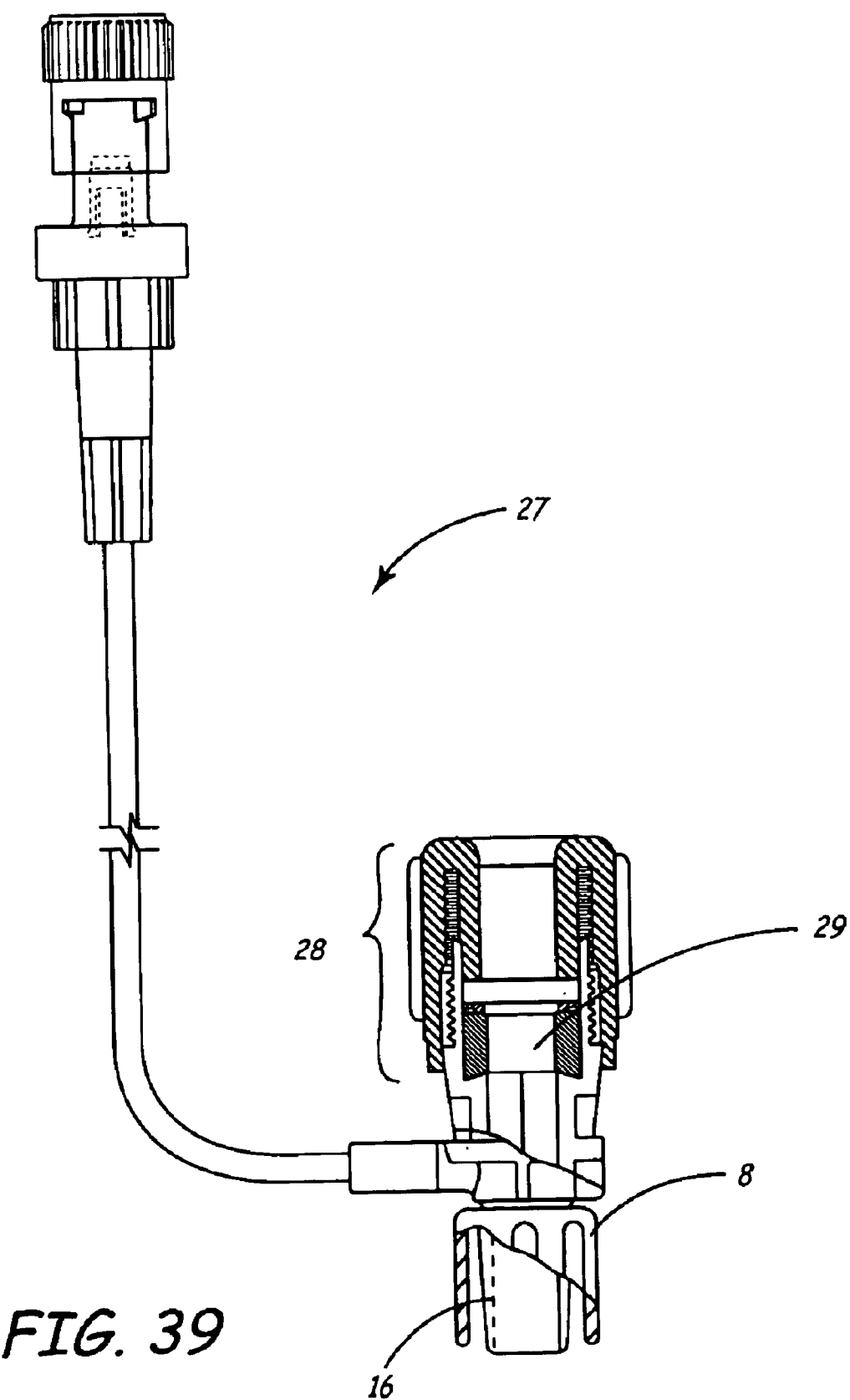
FIG. 39 is partial section plan view of a hemostasis valve according to the present invention.

FIG. 39 is partial section plan view of a hemostasis valve according to the present invention. As illustrated in FIG. 39, in order to enable hemostasis valve 27 to be removed from lead 35, 40 by being slid over connector 50, hemostasis valve 27 of the present invention includes a nonstandard Touhy Borst valve 28 having an adjustable lumen 29 and a non-standard male luer fitting 16 within a locking collar 8. According to the present invention, a minimum internal diameter of adjustable lumen 29 is small enough to seal on lead body 63, approximately 0.050 inches in diameter, and a maximum internal diameter of adjustable lumen is approximately 0.2 inches in diameter. Furthermore, an inner diameter (shown with dashed line) of nonstandard male luer fitting 16 is approximately 0.2 inches. Both the maximum diameter of adjustable lumen 29 and inner diameter of male luer fitting 16 are large enough to allow passage of lead anchoring sleeve 77 and lead connector 50 as RHV 27 is removed from delivery sheath 21, 23.

Returning to FIG. 38, according to the present invention, stylet wire 45 includes knob 48 having a diameter large enough so that knob 48 cannot pass into lumen of lead but small enough so that knob 48 can pass through maximum diameter of adjustable lumen 29 of Touhy Borst valve 28 and inner diameter of male luer fitting 16.

Figure 40:
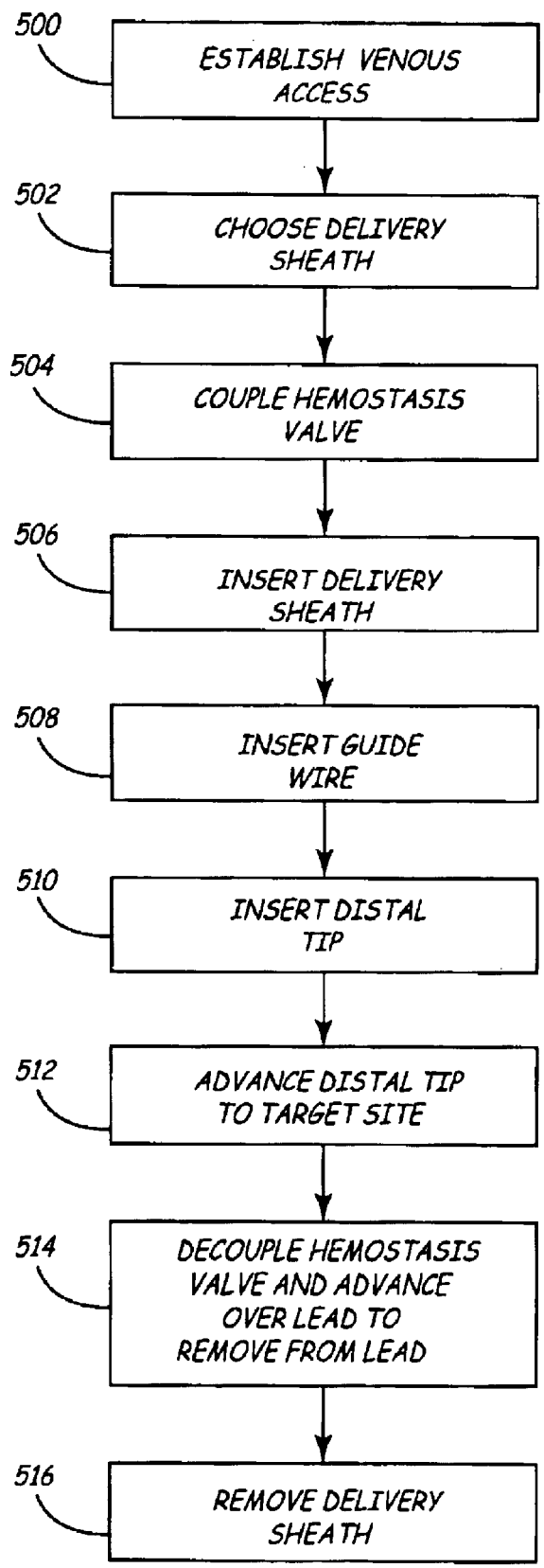
FIG. 40 is a flowchart of a method of delivering a medical electrical lead within a coronary sinus according to the present invention.

FIG. 40 is a flowchart of a method of delivering a medical electrical lead within a coronary sinus according to the present invention. As illustrated in FIG. 40, a method of delivering a medical electrical lead within a coronary sinus according to the present invention includes establishing venous access, Step 500. Once venous access is established, a delivery sheath is chosen corresponding to the desired approach to the coronary sinus, Step 502. For example, if a right-sided approach is preferred, delivery sheath 21 is chosen, and if a left-sided approach is preferred, delivery sheath 23 would be chosen. Rotatable hemostasis valve 27 is coupled at proximal portion 14 of delivery sheath 21 or 23, Step 504, and delivery sheath 21 or 23 is inserted within the venous access over guide wire 4 of tool kit 5, Step 506. Once guide wire 46 is inserted within lead lumen 34, 32 of distal tip 41, 30 of lead 35, 40, respectively, Step 508 and a distal tip 41, 30 of lead 35, 40 is inserted through hemostasis valve 27 and within the delivery sheath 21 or 23, Step 510, distal tip 41, 30 is advanced to a target site within the coronary venous system using guide wire or stylet wire 45 or both, Step 512. Once distal tip 41, 30 of lead 35, 40 is advanced using guide wire 46 and/or stylet wire 45 to position distal tip 41, 30 at the target site, hemostasis valve 27 is decoupled from hub 25 of delivery sheath 21, 23 and advanced over connector 50 of lead 35, 40 in order to remove hemostasis valve 27 from lead 35, 40, Step 516. Delivery sheath 21, 23 is subsequently removed from the venous system, Step 518, using known slitting techniques, for example.

In addition, according to the present invention, when either stylet wire 45 is utilized to guide delivery of distal tip 41, 30 or anchoring sleeve 77 is utilized, alone, or in combination, hemostasis valve 27 of the present invention is also advanced over the utilized inserted stylet wire 45 and/or anchoring sleeve 77. Furthermore, if loading tool 51 is utilized to load stylet wire 45 within lead 35 or 40 or to load guide wire within lead 40, hemostasis valve 27 is also advanced over loading tool 51.

The method of delivering a medical electrical lead within a coronary sinus according to the present invention may also include obtaining a venogram using balloon catheter 200, as described above.

Many alterations and modifications may be made by those having ordinary skill in the art without departing from the spirit and scope of the invention. The illustrated variations have been used only for the purposes of clarity and should not be taken as limiting the invention as defined by the following claims. For example, although delivery sheaths 21, 23 are described with distal portions 12, 13 illustrated in FIG. 13, combinations of delivery sheaths with other styles of distal curvature that are well known in the art, such as Judkins and Amplatz, may be included in alternative embodiments of tool kit 10.

We claim:

1. A method of delivering a medical electrical lead within a coronary venous system, comprising the steps of:
    establishing venous access to the coronary venous system using an introducer tool kit;
    choosing a delivery sheath from a plurality of delivery sheaths corresponding to a desired approach to a coronary sinus of the coronary venous system;
    coupling a hemostasis valve over a proximal portion of the delivery sheath;
    positioning the delivery sheath within the venous access;
    inserting a guide wire within a lead lumen at a distal tip of the medical electrical lead;
    inserting the distal tip of the medical electrical lead through the hemostasis valve and within the delivery sheath;
    guiding advancement of the distal tip of the medical electrical lead to a target site within the coronary venous system using the guide wire; and
    decoupling the hemostasis valve from the delivery sheath and advancing the hemostasis valve over a connector of the medical electrical lead to remove the hemostasis valve from the medical electrical lead.

2. The method of delivering a medical electrical lead within a coronary venous system according to claim 1, wherein the guide wire is a stylet having a stylet knob, and the step of decoupling the hemostasis valve includes advancing the hemostasis valve over the stylet knob to remove the hemostasis valve from the medical electrical lead.

3. The method of delivering a medical electrical lead within a coronary venous system according to claim 2, further comprising the step of fixedly engaging the connector within a loading tool, wherein the step of inserting the guide wire includes loading the stylet wire within the lead lumen using the loading device, and wherein the step of decoupling the hemostasis valve includes advancing the hemostasis valve over the loading tool to remove the hemostasis valve from the medical electrical lead.

4. The method of delivering a medical electrical lead within a coronary venous system according to claim 1, wherein the step of decoupling the hemostasis valve includes advancing the hemostasis valve over an anchoring sleeve positioned on the lead.

5. The method of delivering a medical electrical lead within a coronary venous system according to claim 1, wherein the step of positioning the delivery sheath includes inserting the delivery sheath within the coronary venous system using one of a steerable catheter and an introducer guide wire.

6. The method of delivering a medical electrical lead within a coronary venous system according to claim 5, further comprising the step of securing excess length of one of the guide wire and the introducer guide wire to prevent the excess length from entering a sterile field while allowing repositioning of the guide wire and the introducer guide wire.

7. The method of delivering a medical electrical lead within a coronary venous system according to claim 1, wherein the connector is an IS-1 connector.

8. The method of delivering a medical electrical lead within a coronary venous system according to claim 1, wherein the plurality of delivery sheaths include a left-sided venous access delivery sheath and a right-sided delivery sheath.

9. The method of delivering a medical electrical lead within a coronary venous system according to claim 1 wherein the medical electrical lead is one of an over-the-wire lead and a side-lumen lead.

10. The method of delivering a medical electrical lead within a coronary venous system according to claim 1, further comprising the step of inserting a balloon catheter within the delivery sheath to obtain a venogram to guide advancement of the guide wire and the lead to the target site.

11. A system for delivering a medical electrical lead within a coronary venous system, the medical electrical lead extending from a connector to a distal tip and having a lead lumen located at the distal tip, the system comprising:

an introducer kit establishing venous access to the coronary venous system;

a plurality of delivery sheaths, each corresponding to a desired approach to a coronary sinus of the coronary venous system and insertable within the coronary venous system through the navigation pathway;

an anchoring sleeve positioned along the medical electrical lead;

a hemostasis valve coupled to a delivery sheath of the plurality of delivery sheaths; and a guide wire insertable within the lead lumen, guiding delivery of the distal tip of the medical electrical lead to a target site within the coronary venous system though the hemostasis valve and the delivery sheath, wherein, subsequent to the distal tip being delivered to the target sight, the hemostasis valve is advanced over the connector and the anchoring sleeve of the medical electrical lead to remove the hemostasis valve from the medical electrical lead.

12. The system of claim 11, wherein the guide wire is a stylet having a stylet knob, and the hemostasis valve is advanced over the stylet knob to remove the hemostasis valve from the medical electrical lead.

13. The system of claim 12, further comprising a loading device fixedly engaged with the connector to load the stylet wire within the lead lumen, wherein the hemostasis valve is advanced over the loading tool to remove the hemostasis valve from the medical electrical lead.

14. The system of claim 13, wherein the connector is an IS-1 connector.

15. The system of claim 14, wherein the tool kit includes a steerable catheter and an introducer guide wire, and wherein the delivery sheath is inserted within the coronary venous system through the navigation pathway using one of the steerable catheter and the introducer guide wire.

16. The system of claim 15, further comprising a guide wire clip capable of being positioned in one of a non-engaging open position and an engaging closed position, the guide wire clip securing excess length of one of the guide wire and the introducer guide wire to prevent the guide wire and the introducer guide wire from entering a sterile field while allowing repositioning of the guide wire and the introducer guide wire when the guide wire clip is in the closed position.

17. The system of claim 16, wherein the plurality of delivery sheaths include a left-sided venous access delivery sheath and a right-sided delivery sheath.

18. The system of claim 17, wherein the medical electrical lead is one of an over-the-wire lead and a side-lumen lead.

* * * * *